(12) United States Patent
Klug et al.

(10) Patent No.: US 9,526,687 B2
(45) Date of Patent: Dec. 27, 2016

(54) POLYMERS BASED ON SULFONIC ACIDS, AMIDES AND SPECIAL CROSS-LINKING AGENTS

(75) Inventors: Peter Klug, Grossostheim (DE); Dirk Fischer, Klein-Winternheim (DE); Thomas Lindner, Wiesbaden (DE); Wiebke Mueckenheim, Bad Soden (DE); Bianca Brasch, Aura im Sinngrund (DE); Michael Hornung, Frankfurt am Main (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 117 days.

(21) Appl. No.: 14/003,379

(22) PCT Filed: Mar. 3, 2012

(86) PCT No.: PCT/EP2012/000968
§ 371 (c)(1),
(2), (4) Date: Dec. 11, 2013

(87) PCT Pub. No.: WO2012/119746
PCT Pub. Date: Sep. 13, 2012

(65) Prior Publication Data
US 2014/0086854 A1    Mar. 27, 2014

(30) Foreign Application Priority Data
Mar. 8, 2011 (DE) .......................... 10 2011 013 341

(51) Int. Cl.
| | | |
|---|---|---|
| C08F 220/38 | (2006.01) |
| A61K 8/81 | (2006.01) |
| A61K 31/19 | (2006.01) |
| A61K 31/192 | (2006.01) |
| A61K 31/375 | (2006.01) |
| A61K 31/60 | (2006.01) |
| A61K 47/32 | (2006.01) |
| A61Q 5/06 | (2006.01) |
| A61Q 17/04 | (2006.01) |
| A61Q 19/00 | (2006.01) |
(Continued)

(52) U.S. Cl.
CPC ........... *A61K 8/8188* (2013.01); *A61K 8/8158* (2013.01); *A61K 8/8194* (2013.01); *A61K 31/19* (2013.01); *A61K 31/192* (2013.01); *A61K 31/375* (2013.01); *A61K 31/60* (2013.01); *A61K 47/32* (2013.01); *A61Q 5/06* (2013.01); *A61Q 17/04* (2013.01); *A61Q 19/00* (2013.01); *C08F 220/38* (2013.01); *C08F 220/56* (2013.01); *C08F 220/58* (2013.01); *A61K 9/0014* (2013.01); *A61K 2800/28* (2013.01); *A61K 2800/48* (2013.01); *A61Q 1/02* (2013.01); *A61Q 1/14* (2013.01); *A61Q 5/02* (2013.01); *A61Q 5/04* (2013.01); *A61Q 5/08* (2013.01); *A61Q 5/10* (2013.01); *A61Q 15/00* (2013.01); *A61Q 19/02* (2013.01); *A61Q 19/04* (2013.01); *A61Q 19/08* (2013.01); *A61Q 19/10* (2013.01); *C08F 220/54* (2013.01); *C08F 222/385* (2013.01); *C08F 226/06* (2013.01); *C08F 226/08* (2013.01); *C08F 226/10* (2013.01); *C08F 2220/382* (2013.01); *C08F 2220/387* (2013.01); *C08F 2220/585* (2013.01); *C08F 2222/1026* (2013.01)

(58) Field of Classification Search
CPC .. A61K 8/8188; A61K 8/8194; A61K 8/8158; C08F 220/58; C08F 220/38; C08F 220/56; C08F 220/54; C08F 2220/387; C08F 2220/382; C08F 2220/585; C08F 222/385; C08F 2222/1026; C08F 226/10; C08F 226/06; C08F 226/08
See application file for complete search history.

(56) References Cited

U.S. PATENT DOCUMENTS

| | | |
|---|---|---|
| 5,185,395 A | 2/1993 | Robinson et al. |
| 5,879,718 A | 3/1999 | Sebillote-Arnaud |
(Continued)

FOREIGN PATENT DOCUMENTS

| | | |
|---|---|---|
| CA | 2 209 060 | 12/1997 |
| DE | 10 2009 014877 | 9/2009 |
(Continued)

OTHER PUBLICATIONS

International Search Report for PCT/EP2010/001755, dated May 21, 2010.
(Continued)

*Primary Examiner* — Ling Choi
*Assistant Examiner* — David L Miller
(74) *Attorney, Agent, or Firm* — Tod A. Waldrop

(57) ABSTRACT

The invention relates to water-soluble or water-swellable polymers that contain a) 20.0 to 98.97 mole-% of one or more repeating structural units originating from special monomers with sulfonic acid groups or the salts thereof such as e.g. 2-acrylamido-2-methyl-propanesulfonic acid or the salts thereof, b) 1.0 to 60.0 mole-% of one or more repeating structural units containing an amide group and d) 0.01 to 8.0 mole-% of one or more repeating structural units originating from special crosslinking agents with at least three polymerizable double bonds. The polymers for example have an advantageous sensory property profile and are highly suitable as thickening agents even in salt-containing compositions. They are furthermore advantageously suitable for producing cosmetic, dermatological or pharmaceutical compositions.

22 Claims, No Drawings

(51) Int. Cl.

| | | |
|---|---|---|
| *C08F 220/56* | (2006.01) |
| *C08F 222/38* | (2006.01) |
| *C08F 220/58* | (2006.01) |
| *C08F 220/54* | (2006.01) |
| *C08F 222/10* | (2006.01) |
| *C08F 226/10* | (2006.01) |
| *C08F 226/06* | (2006.01) |
| *C08F 226/08* | (2006.01) |
| *A61K 9/00* | (2006.01) |
| *A61Q 1/02* | (2006.01) |
| *A61Q 1/14* | (2006.01) |
| *A61Q 5/02* | (2006.01) |
| *A61Q 5/04* | (2006.01) |
| *A61Q 5/08* | (2006.01) |
| *A61Q 5/10* | (2006.01) |
| *A61Q 15/00* | (2006.01) |
| *A61Q 19/02* | (2006.01) |
| *A61Q 19/04* | (2006.01) |
| *A61Q 19/08* | (2006.01) |
| *A61Q 19/10* | (2006.01) |

(56) References Cited

U.S. PATENT DOCUMENTS

| | | | |
|---|---|---|---|
| 5,891,452 | A | 4/1999 | Sebillote-Arnaud et al. |
| 5,952,395 | A | 9/1999 | Lorant |
| 6,120,780 | A | 9/2000 | Dupuis et al. |
| 6,180,118 | B1 | 1/2001 | Maubru |
| 6,437,068 | B2 | 8/2002 | Loeffler et al. |
| 6,468,549 | B1 | 10/2002 | Dupuis et al. |
| 6,509,024 | B2 | 1/2003 | Lorant |
| 6,596,264 | B2 | 7/2003 | Terren et al. |
| 2003/0108497 | A1 | 6/2003 | Chevalier et al. |
| 2006/0269490 | A1* | 11/2006 | Braun ............... A61K 8/06 424/59 |
| 2007/0166269 | A1 | 7/2007 | Cassin et al. |
| 2008/0014154 | A1 | 1/2008 | Mougin et al. |
| 2011/0097645 | A1* | 4/2011 | Van Baak et al. ............ 429/492 |
| 2011/0110878 | A1 | 5/2011 | Knappe et al. |
| 2011/0224361 | A1* | 9/2011 | Daniel ............... C08F 220/06 524/556 |
| 2012/0100084 | A1 | 4/2012 | Peter et al. |
| 2014/0127147 | A1 | 5/2014 | Klug et al. |

FOREIGN PATENT DOCUMENTS

| | | | |
|---|---|---|---|
| EP | 0 036 294 | | 10/1981 |
| EP | 0 574 202 | | 12/1993 |
| EP | 0 699 726 | | 3/1996 |
| EP | 0 816 403 | | 1/1997 |
| EP | 0 815 828 | | 1/1998 |
| EP | 0 815 843 | | 1/1998 |
| EP | 0 815 844 | | 1/1998 |
| EP | 0 815 845 | | 1/1998 |
| EP | 0 815 846 | | 1/1998 |
| EP | 0 815 847 | | 1/1998 |
| EP | 0 829 258 | | 3/1998 |
| EP | 1 116 733 | | 7/2001 |
| EP | 1 136 058 | | 9/2001 |
| EP | 1 325 729 | | 9/2003 |
| EP | 1 468 670 | | 10/2004 |
| EP | 1746114 | * | 4/2005 |
| EP | 1 746 114 | | 1/2007 |
| FR | 2 910 899 | | 7/2008 |
| WO | WO 90/12822 | | 11/1990 |
| WO | WO 2010/009953 | | 1/2010 |
| WO | WO 2010057912 A1 | * | 5/2010 ............ C08F 220/06 |

OTHER PUBLICATIONS

Translation of the International Preliminary Report on Patentability for PCT/EP2010/001755, dated Sep. 27, 2011.
Translation of the Written Opinion of the international Searching Authority for PCT/EP2010/001755, dated Sep. 27, 2011.
Safety Data Sheet for "BETA-C", Bimax Chemicals Ltd., London. United Kingdom, Mar. 8, 2011.
English Abstract for EP 0 699 726, Mar. 6, 1998.
English Abstract for EP 1 325 729, Sep. 7, 2003.
English Abstract for EP 1 468 670, Oct. 20, 2004.
English Abstract for FR 2 910 899, Jul. 4, 2008.
International Search Report for PCT/EP2012/000969. dated Aug. 20, 2012,.
International Search Report for PCT/EP2012/000968, dated Aug. 20, 2012.

* cited by examiner

POLYMERS BASED ON SULFONIC ACIDS, AMIDES AND SPECIAL CROSS-LINKING AGENTS

The present invention relates to polymers based on special monomers with sulfonic acid groups or the corresponding sulfonates such as e.g. 2-acrylamido-2-methylpropanesulfonic acid or its salts, special open-chain acryl-, methacryl- or ethacrylamides and special trifunctional crosslinkers, to a process for producing such polymers, to cosmetic, dermatological or pharmaceutical compositions, comprising one or more such polymers, and to certain uses of such polymers such as e.g. the use of such polymers as sensory additive, thickener or consistency regulator.

Polymers based on 2-acrylamido-2-methylpropanesulfonic acid have established themselves in the market place over recent years as versatile gel formers and thickeners in cosmetic, dermatological and pharmaceutical compositions.

For example, EP 0 816 403 (Clariant) describes water-soluble or water-swellable polymers based on 2-acrylamido-2-methylpropanesulfonates. The crosslinking monomers specified are dipropylene glycol diallyl ether, polyglycol diallyl ether, triethylene glycol divinyl ether, hydroquinone diallyl ether, tetraallyloxyethane, tetraethylene glycol diacrylate, triallylamine, trimethylolpropane diallyl ether, methylenebisacrylamide, divinylbenzene, trimethylolpropane triacrylate (TMPTA) and trimethylolpropane trimethacrylate (TMPTMA).

These polymers swell in water over a wide pH range and are easy to handle. They have found a wide field of application in the cosmetics industry, as described for example in EP 0 815 843, EP 0 815 844, EP 0 815 845, EP 0 815 846, EP 0 815 847, EP 0 815 828, EP 0 829 258, EP 1 136 058, EP 1 325 729 and EP 1 468 670 (L'Oréal).

WO 2010/108634 (Clariant) describes, for example, crosslinked polymers comprising structural units derived from 2-acrylamido-2-methylpropanesulfonic acid or from its salts and carboxyethyl acrylate. The polymers are suitable specifically as thickeners and stabilizers on account of the build-up of a yield point in surfactant-containing compositions.

EP 1 746 114 (Shiseido) describes e.g. crosslinked polymers of structural units derived from 2-acrylamido-2-methylpropanesulfonic acid or from its salts and hydroxyethylacrylamide. The crosslinking monomers specified are ethylene glycol diacrylate, ethylene glycol dimethacrylate, polyoxyethylene diacrylate, polyoxyethylene dimethacrylate, diethylene glycol dimethacrylate, trimethylolpropane triacrylate, N,N-methylenebisacrylamide, N,N-ethylenebisacrylamide, triallyl isocyanurate and pentaerythritol dimethacrylate.

WO 2010/009953 (Henkel) describes for example styling compositions comprising crosslinked polymers of 2-acrylamido-2-methylpropanesulfonic acid or its salts, dimethylacrylamide and acrylic acid.

EP 1 116 733 (Clariant) describes e.g. crosslinked polymers comprising structural units derived from 2-acrylamido-2-methylpropanesulfonic acid or its salts and vinylamides. The polymers have an excellent, fresh skin feel and low stickiness. The crosslinking monomers specified are allyl acrylate, allyl methacrylate, dipropylene glycol diallyl ether, polyglycol diallyl ether, triethylene glycol divinyl ether, hydroquinone diallyl ether, tetraallyloxyethane, tetraethylene glycol diacrylate, triallylamine, trimethylolpropane diallyl ether, N,N-methylenebisacrylamide, divinylbenzene and trimethylolpropane triacrylate. However, the described polymers are in need of improvement in respect of their long-term care effect.

Crosslinked polymers of 2-acrylamido-2-methylpropanesulfonic acid and its salts and a dialkylacrylamide are known from JP 2005/206607 (Shiseido). The crosslinking monomers specified are ethylene glycol diacrylate, ethylene glycol dimethacrylate, polyoxyethylene diacrylate, polyoxyethylene dimethacrylate, diethylene glycol dimethacrylate, trimethylolpropane triacrylate, N,N-methylenebisacrylamide, N,N-ethylenebisacrylamide, triallyl isocyanurate and pentaerythritol dimethacrylate.

However, not all sensory property profiles in cosmetic, dermatological or pharmaceutical compositions can be covered with the aforementioned crosslinked polymers and, moreover, their thickening performance in the presence of salt is often in need of improvement.

It was therefore an object of the present invention to provide polymers which, especially in cosmetic, dermatological and pharmaceutical compositions, produce a sensorily optimized property profile, such as e.g. a rich, caring skin feel and, moreover, are advantageously suitable as thickeners even in salt-containing compositions such as in salt-containing compositions comprising water.

Surprisingly, it has been found that this object is achieved with polymers based on special monomers with sulfonic acid groups or their salts of formula (1) below, such as e.g. 2-acrylamido-2-methylpropanesulfonic acid or sulfonates, special open-chain amides of formula (2) below and special trifunctional crosslinkers of formula (5) below.

The invention therefore provides water-soluble or water-swellable polymers comprising:
a) 20.0 to 98.97 mol %, preferably 40.0 to 97.7 mol % and particularly preferably 60.0 to 93.75 mol %, of one or more structural units, recurring independently of one another, of the formula (1)

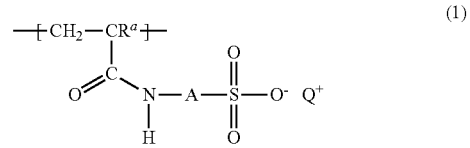

in which
$R^a$ is hydrogen, methyl or ethyl,
A is linear or branched $C_1$-$C_{12}$-alkylene and preferably linear or branched $C_1$-$C_8$-alkylene, and
$Q^+$ is a counterion,
and
b) 1.0 to 60.0 mol %, preferably 2.0 to 39.9 mol % and particularly preferably 5.0 to 29.5 mol %, of one or more structural units, recurring independently of one another, of the formula (2)

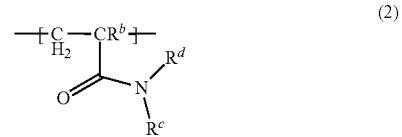

in which $R^b$ is hydrogen, methyl or ethyl, $R^c$ is hydrogen, a linear or branched alkyl group having 1 to 50, preferably 1 to 10 and particularly preferably 1 to 6, carbon atoms, a linear or branched mono-hydroxyalkyl group having 2 to 6 and preferably 2 to 5 carbon atoms or a linear or branched di-hydroxyalkyl group having 2 to 6 and preferably 2 to 5 carbon atoms and $R^d$ is a linear or branched alkyl group having 1 to 50, preferably 1 to 10 and particularly preferably 1 to 6, carbon atoms, a linear or branched mono-hydroxyalkyl group having 2 to 6 and preferably 2 to 5 carbon atoms or a linear or branched di-hydroxyalkyl group having 2 to 6 and preferably 2 to 5 carbon atoms, and d) 0.01 to 8.0 mol %, preferably 0.1 to 5.0 mol % and particularly preferably 0.25 to 3.0 mol %, of one or more crosslinking structural units, recurring independently of one another, of the formula (5)

$$R^{2b}C-Y_2-[E]_p-X-CR^1 \quad H_2C-[D]_o-Y_1-CR^{2a} \quad (5)$$
(with CH₂ branches and $[F]_q$—$Y_3$—$[CH_2-CR^{2c}]$ structure)

in which $R^1$ is hydrogen, methyl, ethyl, methylol (—CH₂—OH) or ethylol (—CH₂—CH₂—OH), $R^{2a}$, $R^{2b}$ and $R^{2c}$, in each case independently of one another, are hydrogen, methyl or ethyl, X is a chemical bond, methylene (—CH₂—), ethylene (—CH₂—CH₂—) or a linear or branched alkylene group having 3 carbon atoms, $Y_1$, $Y_2$ and $Y_3$, in each case independently of one another, are a chemical bond, O, CH₂, C(O)O, OC(O), C(O)NR³ or NR³C(O), $R^3$ is hydrogen or a linear or branched alkyl radical having 1 to 50 carbon atoms, D, E and F, in each case independently of one another, are methyleneoxy, ethyleneoxy, propyleneoxy, a linear or branched alkylene group having 1 to 6 carbon atoms, a linear or branched, mono- or polyunsaturated alkenylene group having 2 to 6 carbon atoms, a linear or branched mono-hydroxyalkylene group having 2 to 6 carbon atoms or a linear or branched di-hydroxyalkylene group having 3 to 6 carbon atoms, o, p and q, in each case independently of one another, are integers from 0 to 50, and the sum o+p+q is ≥3.

In the definitions D, E and F of the structural units of the formula (5), "methyleneoxy" means —CH₂—O— or —O—CH₂—, "ethyleneoxy" means —CH₂—CH₂—O— or —O—CH₂—CH₂—, and "propyleneoxy" means —CH(CH₃)—CH₂—O—, —CH₂—CH(CH₃)—O—, —O—CH(CH₃)—CH₂— or —O—CH₂—CH(CH₃)—.

The amounts (in mol %) given within the context of the present invention for the structural units of the formulae (1), (2) and (5) [and also for the structural units of the formulae (3) and (4) described later on] refer to the total amount of all recurring structural units present in the polymers according to the invention.

In a polymer according to the invention, different structural units of the formula (1) and/or of the formula (2) and/or of the formula (5) may be present in each case.

The polymers according to the invention are exceptionally suitable inter alia as thickeners of aqueous systems and as consistency regulators, in particular in cosmetic, dermatological or pharmaceutical compositions. Compared to polymers from the prior art, they exhibit in particular a more caring skin feel. Moreover, they also bring about a higher viscosity, especially in salt-containing compositions such as e.g. in salt-containing compositions comprising water. Moreover, they exhibit an advantageous salt stability. Moreover, they also have an advantageous long-term care effect. Moreover, they advantageously exhibit good thickening properties over a wide pH range, i.e. even at strongly acidic pH values.

In the one or more structural units of the formula (1) of the polymers according to the invention, $R^a$ is preferably hydrogen or methyl and particularly preferably hydrogen.

In the one or more structural units of the formula (1) of the polymers according to the invention, A is preferably a structural unit of the formula —C(CH₃)₂—CH₂—.

The one or more structural units of the formula (1) of the polymers according to the invention is or are particularly preferably derived from 2-acrylamido-2-methylpropanesulfonic acid or its salts.

As already mentioned, various structural units of the formula (1) may for example be present in a polymer according to the invention. A polymer according to the invention can comprise for example a plurality of structural units of the formula (1) which differ from one another by virtue of differing counterions Q.

In the one or more structural units of the formula (1) of the polymers according to the invention, the counterion $Q^+$ is preferably $H^+$, $NH_4^+$, organic ammonium ions $[HNR^5R^6R^7]^+$, where $R^5$, $R^6$ and $R^7$, independently of one another, can be hydrogen, a linear or branched alkyl group having 1 to 22 carbon atoms, a linear or branched, mono- or polyunsaturated alkenyl group having 2 to 22 carbon atoms, a $C_6$-$C_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals $R^5$, $R^6$ and $R^7$ is not hydrogen, alkali metal⁺, where, among alkali metal⁺, in turn $Li^+$, $Na^+$ and $K^+$ are preferred, ½ alkaline earth metal⁺⁺, where, among ½ alkaline earth metal⁺⁺, in turn ½ $Ca^{++}$ and ½ $Mg^{++}$ are preferred, ½ $Zn^{++}$ or ⅓ $Al^{+++}$ or mixtures of these ions.

In the one or more structural units of the formula (1) of the polymers according to the invention, the counterion $Q^+$ is particularly preferably $H^+$, $NH_4^+$, alkali metal⁺, where, among alkali metal⁺, in turn $Na^+$ is preferred, ½ alkaline earth metal⁺⁺, where, among ½ alkaline earth metal⁺⁺, in turn ½ $Ca^{++}$ and ½ $Mg^{++}$ are preferred, or mixtures of these ions. The counterion $Q^+$ in the one or more structural units of the formula (1) of the polymers according to the invention is particularly preferably selected from the group consisting of $H^+$, $NH_4^+$ and $Na^+$ and, among these, $Q^+$ is preferably in turn selected from the group consisting of $H^+$ and $NH_4^+$.

Preferably, the degree of neutralization of the one or more structural units of the formula (1) of the polymers according to the invention is from 50.0 to 100 mol %, particularly preferably from 80.0 to 100 mol %, especially preferably from 90.0 to 100 mol % and extraordinarily preferably from 95.0 to 100 mol %.

In the one or more structural units of the formula (2) of the polymers according to the invention, $R^b$ is preferably hydrogen or methyl.

In a preferred embodiment of the invention, in the one or more structural units of the formula (2) of the polymers according to the invention, $R^b$ is hydrogen or methyl and preferably hydrogen, $R^c$ is hydrogen, a linear or branched alkyl group having 1 to 6 carbon atoms or a linear or branched mono-hydroxyalkyl group having 2 to 6 carbon atoms and $R^d$ is a linear or branched alkyl group having 1 to 6 carbon atoms or a linear or branched mono-hydroxyalkyl group having 2 to 6 carbon atoms.

In a particularly preferred embodiment of the invention, in the one or more structural units of the formula (2) of the polymers according to the invention, $R^b$ is hydrogen or methyl and preferably hydrogen, $R^c$ is hydrogen or a linear or branched alkyl group having 1 to 6 and preferably 1 to 5 carbon atoms and $R^d$ is a linear or branched alkyl group having 1 to 6 and preferably 1 to 5 carbon atoms or a linear or branched mono-hydroxyalkyl group having 2 to 6 and preferably 2 to 5 carbon atoms.

In a particularly preferred embodiment of the invention, in the one or more structural units of the formula (2), $R^b$ is hydrogen or methyl and preferably hydrogen, $R^c$ is hydrogen, methyl, ethyl, n-propyl or isopropyl and $R^d$ is methyl, ethyl, n-propyl, isopropyl or hydroxyethyl.

Extraordinarily preferably, the one or more structural units of the formula (2) of the polymers according to the invention is or are derived from one or more compounds selected from the group consisting of dimethylacrylamide, hydroxyethylacrylamide and isopropylacrylamide.

In an extraordinarily preferred embodiment of the invention, the polymers according to the invention comprise structural units of the formula (2) derived from dimethylacrylamide. If the polymers according to the invention comprise such structural units, they are present, in one preferred embodiment of the invention among these, in an amount of from 10.0 to 25 mol % in the polymers according to the invention.

In a further extraordinarily preferred embodiment of the invention, the polymers according to the invention comprise structural units of the formula (2) derived from hydroxyethylacrylamide. If the polymers according to the invention comprise such structural units, they are present, in one preferred embodiment of the invention among these, in an amount of from 10.0 to 25 mol % in the polymers according to the invention.

In a further extraordinarily preferred embodiment of the invention, the polymers according to the invention comprise structural units of the formula (2) derived from isopropylacrylamide. If the polymers according to the invention comprise such structural units, they are present, in one preferred embodiment of the invention among these, in an amount of from 10.0 to 25 mol % in the polymers according to the invention.

In a further extraordinarily preferred embodiment of the invention, the polymers according to the invention comprise mixtures of structural units of the formula (2) derived from dimethylacrylamide and hydroxyethylacrylamide. If the polymers according to the invention comprise mixtures of such structural units, these mixtures are present, in one preferred embodiment of the invention among these, in an amount of from 10.0 to 25 mol % in the polymers according to the invention.

In the one or more structural units of the formula (5) of the polymers according to the invention, $R^1$ is preferably hydrogen, ethyl or methylol and particularly preferably hydrogen or ethyl.

In the one or more structural units of the formula (5) of the polymers according to the invention, $R^{2a}$, $R^{2b}$ and $R^{2c}$, in each case independently of one another, are preferably hydrogen or methyl and particularly preferably hydrogen.

In the one or more structural units of the formula (5) of the polymers according to the invention, X is preferably a chemical bond, methylene or ethylene and particularly preferably a chemical bond or methylene.

In the one or more structural units of the formula (5), $Y_1$, $Y_2$ and $Y_3$, in each case independently of one another, are preferably C(O)O, OC(O), C(O)NR$^3$ or NR$^3$C(O) and particularly preferably C(O)O or OC(O).

$R^3$ is preferably hydrogen or a linear or branched alkyl radical having 1 to 10 and preferably 1 to 6 carbon atoms.

In the one or more structural units of the formula (5) of the polymers according to the invention, D, E and F, in each case independently of one another, are preferably methyleneoxy, ethyleneoxy or propyleneoxy and particularly preferably ethyleneoxy or propyleneoxy.

As already mentioned, a polymer according to the invention can for example comprise a plurality of structural units of the formula (5). This plurality of structural units of the formula (5) can differ from one another for example by virtue of the degree of ethoxylation and/or propoxylation.

If, in the structural units -[-D-]$_o$-, -[-E-]$_p$- and -[-F-]$_q$- of the formula (5), one or more of the running numbers o, p or q is an integer >1, the respective structural units can be composed of a single unit or of different units. If, for example, the running number "o"=3, then the structural unit -[-D-]$_o$- can be composed e.g. of 3 ethyleneoxy units. It can then, however, e.g. also be composed of 2 ethyleneoxy units and 1 propyleneoxy unit (or vice versa) or it can then be composed e.g. also from 1 methyleneoxy unit, 1 ethyleneoxy unit and 1 propyleneoxy unit, etc. All other combinations of units within the structural units -[-D-]$_o$-, -[-E-]$_p$- and -[-F-]$_q$- are also possible provided the definition of the groups D, E and F and of the running numbers o, p and q is observed. Within the structural units -[-D-]$_o$-, -[-E-]$_p$- and -[-F-]$_q$-, the distribution of the individual units can be random, alternating, gradient-like or block-like and is preferably random or block-like.

In the one or more structural units of the formula (5) of the polymers according to the invention, the individual structural units -[-D-]$_o$-, -[-E-]$_p$- and -[-F-]$_q$- can be composed from different units as just described. In this case, the corresponding units are preferably selected from the group consisting of methyleneoxy, ethyleneoxy and propyleneoxy and particularly preferably selected from the group consisting of ethyleneoxy and propyleneoxy.

In the one or more structural units of the formula (5) of the polymers according to the invention, o, p and q, in each case independently of one another, are preferably integers from 0 to 30, particularly preferably integers from 0 to 15 and especially preferably integers from 0 to 10.

In the one or more structural units of the formula (5) of the polymers according to the invention, the sum o+p+q is preferably from 3 to 90, particularly preferably from 3 to 45, especially preferably from 3 to 30 and extraordinarily preferably from 3 to 20.

In a preferred embodiment of the invention, the one or more crosslinking structural units of the formula (5) of the polymers according to the invention preferably originate from ethoxylated tri-acrylic or ethoxylated tri-methacrylic acid esters, ethoxylated tri-acryl- or ethoxylated tri-methacrylamides, propoxylated tri-acrylic or propoxylated tri-methacrylic acid esters, propoxylated tri-acryl- or propoxylated tri-methacrylamides, random or blockwise functionalized ethoxylated/propoxylated tri-acrylic or randomly or blockwise functionalized ethoxylated/propoxylated tri-methacrylic acid esters, ethoxylated/propoxylated tri-acryl- or ethoxylated/propoxylated tri-methacrylamides, or other ethoxylated tri-acrylic or ethoxylated tri-methacrylic acid esters, ethoxylated tri-acryl- or ethoxylated tri-methacrylamides of multifunctional alcohols, or other propoxylated tri-acrylic or propoxylated tri-methacrylic acid esters, propoxylated tri-acryl- or propoxylated tri-methacrylamides of multifunctional alcohols, or other random or blockwise functionalized ethoxylated/propoxylated tri-acrylic or ethoxylated/propoxylated tri-methacrylic acid esters, ethoxylated/propoxylated tri-acryl- or ethoxylated/propoxylated tri-methacrylamides of other multifunctional alcohols, or ethoxylated glycerol triacrylates or methacrylates, or propoxylated glycerol triacrylates or methacrylates or other random or blockwise functionalized ethoxylated/propoxylated glycerol triacrylates or methacrylates or ethoxylated glycerol triacrylamides or methacrylamides, or propoxylated glycerol triacrylamides or methacrylamides or other random or blockwise functionalized ethoxylated/propoxylated glycerol triacrylamides or methacrylamides, or ethoxylated trimethylolpropane triacrylates or trimethacrylates or propoxylated trimethylolpropane triacrylates or trimethacrylates or other random or blockwise functionalized ethoxylated/propoxylated trimethylolpropane triacrylates or trimethacrylates or ethoxylated trimethylolpropanetriacrylamides or -trimethacrylamides or propoxylated trimethylolpropanetriacrylamides or -trimethacrylamides or other random or blockwise functionalized ethoxylated/propoxylated trimethylolpropanetriacrylamides or -trimethacrylannides, or ethoxylated pentaerythritol triacrylates or trimethacrylates or propoxylated pentaerythritol triacrylates or trimethacrylates or other random or blockwise functionalized ethoxylated/propoxylated pentaerythritol triacrylates or trimethacrylates or ethoxylated pentaerythritoltriacrylamides or -trimethacrylamides or propoxylated pentaerythritol-triacrylamides or -trimethacrylamides or other random or blockwise functionalized ethoxylated/propoxylated pentaerythritoltriacrylamides or -trimethacrylamides.

In one particularly preferred embodiment of the invention, in the one or more structural units of the formula (5), $R^1$ is hydrogen or ethyl, $R^{2a}$, $R^{2b}$ and $R^{2c}$, in each case independently of one another, are hydrogen or methyl, X is a chemical bond or methylene, $Y_1$, $Y_2$ and $Y_3$, in each case independently of one another, are C(O)O or OC(O), D, E and F, in each case independently of one another, are ethyleneoxy or propyleneoxy, o, p and q, in each case independently of one another, are integers from 0 to 30 and the sum o+p+q is from 3 to 20.

Among these, the polymers according to the invention are in turn preferably built up on the basis of glycerol or on the basis of trimethylolpropane.

Particularly preferred crosslinkers for the polymers according to the invention, i.e. compounds from which the one or more structural units of the formula (5) originate, are glycerol propoxylate triacrylate (3/3 PO/OH; PO=propyleneoxy; 3 mol of propylene oxide were used in the synthesis for 3 mol of OH groups of the glycerol) (GPTA),
glycerol ethoxylate triacrylate (3/3 EO/OH; EO=ethyleneoxy) (GETA),
glycerol propoxylate triacrylate (15/3 PO/OH) ($GP_{15}TA$),
glycerol ethoxylate triacrylate (15/3 EO/OH) ($GE_{15}TA$),
glycerol propoxyethoxylate triacrylate (15/3 PO-EO/OH) (GPETA),
trimethylolpropane propoxy triacrylate (3/3 PO/OH) (TMPTA-PO-3),
trimethylolpropane ethoxy triacrylate (3/3 EO/OH) (TMPTA-EO-3),
trimethylolpropane ethoxy triacrylate (6/3 EO/OH) (TMPTA-EO-6),
trimethylolpropane ethoxy triacrylate (15/3 EO/OH) (TMPTA-EO-15) and
trimethylolpropane propoxyl ethoxy triacrylate (15/3 PO-EO/OH) (TMPTA-PO-EO-15).

Particular preference is given to
glycerol propoxylate triacrylate (GPTA),
glycerol propoxylate triacrylate (15/3 PO/OH) ($GP_{15}TA$),
trimethylolpropane propoxy triacrylate (3/3 PO/OH) (TMPTA-PO-3),
trimethylolpropane ethoxy triacrylate (3/3 EO/OH) (TMPTA-EO-3) and
trimethylolpropane ethoxy triacrylate (15/3 EO/OH) (TMPTA-EO-15).

Glycerol propoxylate triacrylate (GPTA),
trimethylolpropane propoxy triacrylate (3/3 PO/OH) (TMPTA-PO-3) and trimethylolpropane ethoxy triacrylate (3/3 EO/OH) (TMPTA-EO-3) are extraordinarily preferred.

Among these compounds, preference is in turn given to glycerol propoxylate triacrylate (GPTA).

Furthermore, preferred amounts for the one or more structural units of the formula (5) in the polymers according to the invention, in particular for structural units of the formula (5) which originate from the crosslinkers just explicitly specified are 0.25 to 5.0 mol % and particularly preferably 0.5 to 2.0 mol %.

In a further preferred embodiment of the invention, the polymers according to the invention comprise
a) 45.0 to 96.9 mol %, preferably 57.1 to 88.8 mol % and particularly preferably 72.5 to 82.2 mol %, of one or more recurring structural units of the formula (1),
b) 3.0 to 50.0 mol %, preferably 11.0 to 39.9 mol % and particularly preferably 17.5 to 25.0 mol %, of one or more recurring structural units of the formula (2), and
d) 0.1 to 5.0 mol %, preferably 0.2 to 3.0 mol % and particularly preferably 0.3 to 2.5 mol %, of one or more recurring crosslinking structural units of the formula (5).

In a particularly preferred embodiment of the invention, the recurring structural units of the polymers according to the invention consist of one or more recurring structural units of the formula (1), of one or more recurring structural units of the formula (2) and one or more recurring structural units of the formula (5). In a particularly preferred embodiment of the invention, the amounts of structural units of the formulae (1), (2) and (5) in the polymers according to the invention are then as just stated.

In a further preferred embodiment of the invention, the polymers according to the invention comprise 0.01 to 30.0 mol %, preferably 0.1 to 20.0 mol % and particularly preferably 0.5 to 15.0 mol %, of one or more structural units, recurring independently of one another, of the formula (3)

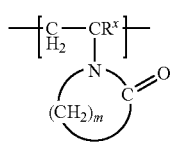

(3)

in which
$R^x$ is hydrogen, methyl or ethyl and
m is an integer from 2 to 9.

In the one or more structural units of the formula (3), $R^x$ is preferably hydrogen or methyl and particularly preferably hydrogen.

In the one or more structural units of the formula (3), m is preferably an integer from 2 to 9, particularly preferably an integer from 2 to 6 and especially preferably m is 3 or 4.

In a particularly preferred embodiment of the invention, the polymers according to the invention comprise structural units of the formula (3) derived from N-vinylpyrrolidone. If the polymers according to the invention comprise such structural units, they are present, in a preferred embodiment of the invention among these, in an amount of from 0.5 to 5.0 mol %, and in a particularly preferred embodiment of the invention among these in an amount of from 0.75 to 2.0 mol % in the polymers according to the invention.

In a further preferred embodiment of the invention, the polymers according to the invention comprise 0.01 to 30.0 mol %, preferably 0.1 to 20.0 mol % and particularly preferably 0.5 to 15.0 mol %, of one or more structural units, recurring independently of one another, of the formula (4)

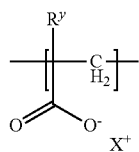

(4)

in which
$R^y$ is hydrogen, methyl or ethyl and
$X^+$ is a counterion.

In the one or more structural units of the formula (4), $R^y$ is preferably hydrogen or methyl and particularly preferably methyl.

In a particularly preferred embodiment of the invention, the polymers according to the invention comprise one or more structural units of the formula (4) derived from methacrylic acid or its salts ($R^y$=methyl). If the polymers according to the invention comprise such structural units, these are present in a preferred embodiment of the invention among these in an amount of from 0.5 to 15.0 mol %, and in a particularly preferred embodiment of the invention among these in an amount of from 1.75 to 13.0 mol % in the polymers according to the invention.

In a polymer according to the invention, in each case different structural units of the formula (3) and/or of the formula (4) may be present.

In a further preferred embodiment of the invention, the polymers according to the invention comprise one or more structural units of the formula (3) and one or more structural units of the formula (4).

In a further particularly preferred embodiment of the invention, the polymers according to the invention comprise mixtures of structural units of the formula (3) derived from N-vinylpyrrolidone and structural units of the formula (4) derived from methacrylic acid or its salts. If the polymers according to the invention comprise mixtures of such structural units, these mixtures are present in a preferred embodiment of the invention among these in an amount of from 1.5 to 7.5 mol %, and in a particularly preferred embodiment of the invention among these in an amount of from 2.5 to 6.5 mol % in the polymers according to the invention.

As already mentioned, different structural units of the formula (4), for example, may be present in a polymer according to the invention. A polymer according to the invention can for example comprise a plurality of structural units of the formula (4) which differ from one another by virtue of different counterions $X^+$.

Preferably, $X^+$ is $H^+$, $NH_4^+$, organic ammonium ions, $[HNR^{5a}R^{6a}R^{7a}]^+$, where $R^{5a}$, $R^{6a}$ and $R^{7a}$, independently of one another can be hydrogen, a linear or branched alkyl group having 1 to 22 carbon atoms, a linear or branched, mono- or polyunsaturated alkenyl group having 2 to 22 carbon atoms, a $C_6$-$C_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals $R^{5a}$, $R^{6a}$ and $R^{7a}$ is not hydrogen, alkali metal$^+$, where among alkali metal$^+$ in turn $Li^+$, $Na^+$ and $K^+$ are preferred, ½ alkaline earth metal$^{++}$, where among ½ alkaline earth metal in turn ½ $Ca^{++}$ and ½ $Mg^{++}$ are preferred, ½ $Zn^{++}$ or ⅓ $Al^{+++}$ or mixtures of these ions.

In the one or more structural units of the formula (4) of the polymers according to the invention, the counterion $X^+$ is particularly preferably selected from the group consisting of $H^+$, $NH_4^+$, alkali metal$^+$, where among alkali metal$^+$ in turn $Na^+$ is preferred, ½ alkaline earth metal$^{++}$, where among ½ alkaline earth metal in turn ½ $Ca^{++}$ and ½ $Mg^{++}$ are preferred, and mixtures of these ions. The counterion $X^+$ is particularly preferably selected from the group consisting of $H^+$, $NH_4^+$ and $Na^+$ and particularly preferably $X^+$ is selected from the group consisting of $H^+$ and $NH_4^+$.

In a further particularly preferred embodiment of the invention, the polymers according to the invention comprise a plurality of structural units of the formula (4), where, in some structural units of the formula (4), the meaning of the counterions $X^+$ is $H^+$ and in the other structural units of the formula (4), the meaning of the counterions $X^+$ is one other than $H^+$ and $X^+$ in these other structural units of the formula (4) is preferably selected from the group consisting of $NH_4^+$ and $Na^+$ and particularly preferably $NH_4^+$.

In a particularly preferred embodiment of the invention, the counterion $Q^+$ in the one or more structural units of the formula (1) of the polymers according to the invention is selected from the group consisting of $H^+$, $NH_4^+$, alkali metal$^+$, where among alkali metal$^+$ in turn $Na^+$ is preferred, ½ alkaline earth metal$^{++}$, where among ½ alkaline earth metal$^{++}$ in turn ½ $Ca^{++}$ and ½ $Mg^{++}$ are preferred, and mixtures of these ions, among these $Q^+$ is preferably selected from the group consisting of $H^+$, $NH_4^+$ and $Na^+$ and in turn among these $Q^+$ is preferably selected from the group consisting of $H^+$ and $NH_4^+$ and in this particularly preferred embodiment of the invention the counterion $X^+$ in the one or more structural units of the formula (4) of the polymers according to the invention is selected from the group consisting of $H^+$, $NH_4^+$, alkali metal$^+$, where among alkali metal$^+$ in turn $Na^+$ is preferred, ½ alkaline earth metal$^{++}$, where among ½ alkaline earth metal$^{++}$ in turn ½ $Ca^{++}$ and ½ $Mg^{++}$ are preferred, and mixtures of these ions, among these $X^+$ is preferably selected from the group consisting of $H^+$, $NH_4^+$ and $Na^+$ and in turn among these $X^+$ is preferably selected from the group consisting of $H^+$ and $NH_4^+$.

In a further particularly preferred embodiment of the invention, $X^+$ in the one or more structural units of the formula (4) is $H^+$. This can also apply for the case where $Q^+$ in the one or more structural units of the formula (1) is a counterion other than $H^+$ or is at least partially a counterion other than $H^+$.

In a further preferred embodiment of the invention, the polymers according to the invention comprise a) 25.0 to 96.9 mol %, preferably 42.0 to 88.8 mol % and particularly preferably 64.5 to 82.2 mol %, of one or more recurring structural units of the formula (1), b) 2.5 to 50.0 mol %, preferably 10.0 to 39.9 mol % and particularly preferably 15.0 to 25.0 mol %, of one or more recurring structural units of the formula (2), c) 0.5 to 20.0 mol %, preferably 1.0 to 15.1 mol % and particularly preferably 2.0 to 8.0 mol %, of one or more recurring structural units of the formula (3) or formula (4) or mixtures of one or more recurring structural units of the formula (3) and formula (4) and d) 0.1 to 5.0 mol %, preferably 0.2 to 3.0 mol % and particularly preferably 0.3 to 2.5 mol %, of one or more recurring crosslinking structural units of the formula (5).

In a particularly preferred embodiment of the invention, the recurring structural units of the polymers according to the invention consist of one or more recurring structural units of the formula (1), one or more recurring structural units of the formula (2), one or more recurring structural units selected from the group consisting of the structural units of the formula (3) and of the formula (4) and one or more recurring structural units of the formula (5). In a particularly preferred embodiment of the invention, the amounts of structural units of the formulae (1), (2), (5) and the amounts of structural units selected from the formulae (3) and (4) in the polymers according to the invention are then as just stated.

If structural units of the formula (3) and of the formula (4) are present in the polymers according to the invention, the molar ratio of the one or more structural units of the formula (3) to the one or more structural units of the formula (4) in one preferred embodiment of the invention among these is from 1:99 to 99:1, in a particularly preferred embodiment of the invention among these from 1:1 to 1:20 and in an especially preferred embodiment of the invention among these from 1:2 to 1:10.

Recurring structural unit present in polymers originate from the polymerizable monomers used for their preparation. The distribution of the different recurring structural units in the polymers according to the invention can be random, blockwise, alternate or gradient-like and is preferably random or gradient-like.

The mass fraction of recurring structural units in the polymers according to the invention, based on the total mass of all structural units chemically bonded in the polymers according to the invention, is preferably greater than or equal to 85% by weight, particularly preferably greater than or equal to 90% by weight, particularly preferably greater than or equal to 95% by weight and extraordinarily preferably greater than or equal to 97% by weight. Chemically bonded structural units which may be present in the polymers according to the invention but do not originate from the polymerizable monomers used for their preparation may be in particular structural units which originate from initiators used for preparing the polymers according to the invention.

In a further preferred embodiment of the invention, the polymers according to the invention are free from structural units of the formula (10)

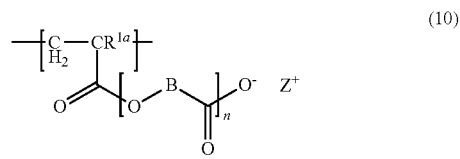

in which $R^{1a}$ is hydrogen, methyl or ethyl, $Z^+$ is a counterion and preferably $H^+$, $NH_4^+$, organic ammonium ions $[HNR^{5b}R^{6b}R^{7b}]^+$, where $R^{5b}$, $R^{6b}$ and $R^{7b}$, independently of one another, can be hydrogen, a linear or branched alkyl group having 1 to 22 carbon atoms, a linear or branched, mono- or polyunsaturated alkenyl group having 2 to 22 carbon atoms, a $C_6$-$C_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals $R^{5b}$, $R^{6b}$ and $R^{7b}$ is not hydrogen, $Na^+$, $K^+$, ½ $Ca^{++}$, ½ $Mg^{++}$, ½ $Zn^{++}$ or ⅓ $Al^{+++}$ or mixtures of these ions, B is a linear or branched alkylene group having 1 to 6 carbon atoms, and n is an integer from 1 to 10.

In a further preferred embodiment of the invention, the polymers according to the invention do not comprise any cationic structural units.

The polymers according to the invention preferably have a molecular weight of from $10^3$ to $10^9$ g/mol, particularly preferably from $10^4$ to $10^7$ g/mol and especially preferably from $10^5$ to $5 \cdot 10^6$ g/mol.

The polymers according to the invention are prepared by means of free-radical polymerization in a protic solvent, preferably in tert-butanol. In this connection, the corresponding monomers are dissolved or dispersed e.g. in the protic solvent and the polymerization is started in a manner known per se, e.g. by adding a radical-forming compound. Starters or initiators which can in principle be used are all substances suitable and known for this purpose, in the customary amounts. In one preferred embodiment of the invention, however, dilauroyl peroxide or dimethyl 2,2'-azobis(2-methylpropionate) (V601) are used as initiator. The amount of initiator for preparing the polymers according to the invention is preferably less than or equal to 10% by weight, particularly preferably less than or equal to 5% by weight and especially preferably less than or equal to 3% by weight, based on the total amount of monomers and initiator used for the polymerization. In this connection, the initially introduced monomers can for example be polymerized "directly". However, they can also be neutralized prior to the polymerization by, for example, reacting acid groups of monomers used with bases prior to the polymerization. Instead of the neutralization of the monomers prior to the polymerization, however, it is also possible to neutralize the polymers with the bases after the polymerization has taken place.

The present invention therefore further provides a process for preparing the polymers according to the invention, wherein monomers from which the structural units of the formula (1), formula (2) and formula (5) are derived, and also optionally further monomers from which, for example, the one or more structural unit selected from the formulae (3) and (4) are derived are free-radically polymerized in a protic solvent, preferably in tert-butanol, and optionally the monomers before the polymerization or the polymer after the polymerization is or are neutralized with a base such as ammonia or organic amines or a base containing alkali metal$^+$, preferably Li$^+$, Na$^+$ or K$^+$, a base containing alkaline earth metal$^{++}$, preferably Ca$^{++}$ or Mg$^{++}$, or a base containing Zn$^{++}$ or Al$^{+++}$. If a neutralization is carried out with bases containing alkali metal$^+$, alkaline earth metal$^{++}$, Zn$^{++}$ or Al$^{+++}$ in a preferred embodiment, it is carried out with the corresponding hydroxides or carbonates and particularly preferably with hydroxides.

Free-radical polymerizations are generally known to the person skilled in the art and are described in detail in standard works of the literature, e.g. in "Makromolekulare Chemie: Eine Einführung" [Macromolecular chemistry: an introduction] by Bernd Tieke, Wiley-VCH, 2$^{nd}$ fully revised and expanded edition (Sep. 9, 2005) ISBN-10: 3527313796.

The polymers according to the invention are characterized by good skin mildness and a pleasant, rich skin feel. They also have advantageous thickening properties, particularly in salt-containing compositions, such as e.g. in salt-containing compositions comprising water, and a high electrolyte stability. Moreover, the polymers according to the invention are acid-stable. Since the polymers according to the invention thicken even at acidic pH values, thickened cosmetic, dermatological or pharmaceutical products can advantageously also be preserved with organic acids, such as benzoic acid, sorbic acid, paramethoxybenzoic acid since adequate thickener performance is available even at the required low pH values. Clear solutions can be obtained therewith.

The polymers according to the invention are advantageously suitable for preparing cosmetic, dermatological or pharmaceutical compositions.

The present invention therefore further provides the use of one or more polymers according to the invention for preparing cosmetic, dermatological or pharmaceutical compositions, and also cosmetic, dermatological or pharmaceutical compositions comprising one or more polymers according to the invention.

The cosmetic, dermatological or pharmaceutical compositions according to the invention comprise the one or more polymers according to the invention preferably in an amount of from 0.01 to 10.0% by weight, particularly preferably in an amount of from 0.1 to 5.0% by weight and particularly preferably in an amount of from 0.25 to 2.0% by weight, in each case based on the total weight of the compositions according to the invention.

In one preferred embodiment of the invention, the cosmetic, dermatological or pharmaceutical compositions according to the invention have viscosities preferably in the range from 100 to 200 000 mPa·s, particularly preferably in the range from 1000 to 100 000 mPa·s, especially preferably in the range from 2000 to 50 000 mPa·s and extraordinarily preferably in the range from 5000 to 30 000 mPa·s (25° C., Brookfield RVT, T-C spindle at 20 revolutions per minute).

In a further preferred embodiment of the invention, the compositions according to the invention are in the form of fluids, gels, foams, sprays, lotions or creams.

The compositions according to the invention are preferably formulated on an aqueous or aqueous-alcoholic basis or are present in the form of emulsions, preferably in the form of oil-in-water emulsions.

In a particularly preferred embodiment of the invention, the compositions according to the invention are in the form of aqueous-alcoholic compositions and preferably comprise, based on the total weight of the compositions, a) up to 90.0% by weight, preferably 19.49 to 80.0% by weight, particularly preferably 23.9 to 70.0% by weight, especially preferably 28.5 to 60.0% by weight, of water, b) up to 90.0% by weight, preferably 19.49 to 80.0% by weight, particularly preferably 28.9 to 75.0% by weight, especially preferably 38.5 to 70.0% by weight, of one or more alcohols, preferably ethanol or isopropanol, c) up to 10.0% by weight, preferably 0.01 to 10.0% by weight, particularly preferably 0.1 to 5.0% by weight, especially preferably 0.5 to 2.0% by weight, of one or more of the polymers according to the invention and d) up to 20.0% by weight, preferably 0.5 to 10.0% by weight, particularly preferably 1.0 to 5.0% by weight, especially preferably 1.0 to 3.0% by weight, of one or more further additives.

Preferably, the one or more further additives in the aqueous-alcoholic compositions just mentioned is or are selected from the group consisting of surfactants and antimicrobial active ingredients. In a preferred embodiment of the invention, such as e.g. in the case just mentioned, the compositions according to the invention are in the form of disinfection gels.

In a further particularly preferred embodiment of the invention, the compositions according to the invention are in the form of oil-in-water emulsions and preferably comprise, based on the total weight of the compositions, a) up to 95.0% by weight, preferably 49.49 to 95.0% by weight, particularly preferably 68.9 to 90.0% by weight, especially preferably 70.0 to 85.0% by weight, of a water phase or aqueous-alcoholic phase, b) up to 70.0% by weight, preferably 4.49 to 50.0% by weight, particularly preferably 8.9 to 30.0% by weight, especially preferably 13.5 to 25.0% by weight, of an oil phase, c) up to 10.0% by weight, preferably 0.01 to 10.0% by weight, particularly preferably 0.1 to 5.0% by weight, especially preferably 0.5 to 2.0% by weight, of one or more of the polymers according to the invention and d) up to 20.0% by weight, preferably 0.5 to 10% by weight, particularly preferably 1.0 to 5.0% by weight, especially preferably 1.0 to 3.0% by weight, of one or more further additives.

Preferably, the one or more further additives in the oil-in-water emulsions just mentioned is or are selected from the group consisting of emulsifiers, coemulsifiers, solubilizers, active substances, sun protection filters, pigments and antimicrobial active ingredients.

All monohydric or polyhydric alcohols are suitable for the compositions according to the invention on an aqueous-alcoholic basis or alcoholic basis. Preference is given to using alcohols having 1 to 4 carbon atoms such as ethanol, propanol, isopropanol, n-butanol, isobutanol, tert-butanol or glycerol, and also alkylene glycols, in particular propylene glycol, butylene glycol or hexylene glycol, and mixtures of said alcohols. Further preferred alcohols are polyethylene glycols with a relative molecular mass below 2000. Particular preference is given to using ethanol or isopropanol.

The compositions according to the invention can comprise one or more oils.

The oils can advantageously be selected from the groups of triglycerides, natural and synthetic fatty bodies, preferably esters of fatty acids with alcohols of low carbon number, e.g. with methanol, isopropanol, propylene glycol or glycerol, or esters of fatty alcohols with alkanoic acids of low carbon number or with fatty acids or from the group of alkylbenzoates, and also natural or synthetic hydrocarbon oils.

Of suitability are triglycerides of linear or branched, saturated or unsaturated, optionally hydroxylated, $C_8$-$C_{30}$-fatty acids, in particular vegetable oils, such as sunflower oil, corn oil, soybean oil, rice oil, jojoba oil, babussu oil, pumpkin oil, grape seed oil, sesame oil, walnut oil, apricot oil, orange oil, wheat germ oil, peach kernel oil, macadamia oil, avocado oil, sweet almond oil, lady's smock oil, castor oil, olive oil, peanut oil, rapeseed oil and coconut oil, and also synthetic triglyceride oils, e.g. the commercial product Myritol® 318. Hydrogenated triglycerides are also preferred in accordance with the invention. Oils of animal origin, for example beef tallow, perhydrosqualene, lanolin, can also be used.

A further class of preferred oil bodies are the benzoic acid esters of linear or branched $C_{8-22}$-alkanols, e.g. the commercial products Finsolv®SB (isostearyl benzoate), Finsolv®TN($C_{12}$-$C_{15}$-alkyl benzoate) and Finsolv®EB (ethylhexyl benzoate).

A further class of preferred oil bodies are the dialkyl ethers having in total 12 to 36 carbon atoms, in particular having 12 to 24 carbon atoms, such as e.g. di-n-octyl ether (Cetiol® OE), di-n-nonyl ether, di-n-decyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether, di-3-ethyldecyl ether, tert-butyl n-octyl ether, isopentyl n-octyl ether and 2-methylpentyl n-octyl ether, and di-tert-butyl ether and diisopentyl ether.

Likewise of suitability are branched saturated or unsaturated fatty alcohols having 6-30 carbon atoms, e.g. isostearyl alcohol, and also Guerbet alcohols.

A further class of preferred oil bodies is hydroxycarboxylic acid alkyl esters. Preferred hydroxycarboxylic acid alkyl esters are full esters of glycolic acid, lactic acid, malic acid, tartaric acid or citric acid. Further esters of hydroxycarboxylic acids which are suitable in principle are esters of β-hydroxypropionic acid, of tartronic acid, of D-gluconic acid, sugar acid, mucic acid or glucuronic acid. Suitable alcohol components of these esters are primary, linear or branched aliphatic alcohols having 8 to 22 carbon atoms. In this connection, the esters of $C_{12}$-$C_{15}$-fatty alcohols are particularly preferred. Esters of this type are commercially available, e.g. under the trade name Cosmacol® from EniChem, Augusta Industriale.

A further class of preferred oil bodies is dicarboxylic acid esters of linear or branched $C_2$-$C_{10}$-alkanols, such as di-n-butyl adipate (Cetiol® B), di-(2-ethylhexyl) adipate and di-(2-ethylhexyl) succinate, and also diol esters such as ethylene glycol dioleate, ethylene glycol diisotridecanoate, propylene glycol di-(2-ethylhexanoate), propylene glycol diisostearate, propylene glycol dipelargonate, butanediol diisostearate and neopentyl glycol dicaprylate, and also diisotridecyl azelate.

Likewise preferred oil bodies are symmetrical, asymmetrical or cyclic esters of carbonic acid with fatty alcohols, glycerol carbonate or dicaprylyl carbonate (Cetiol® CC).

A further class of preferred oil bodies is the esters of dimers of unsaturated $C_{12}$-$C_{22}$-fatty acids (dimer fatty acids) with monohydric linear, branched or cyclic $C_2$-$C_{18}$-alkanols or with polyhydric linear or branched $C_2$-$C_6$-alkanols.

A further class of preferred oil bodies is hydrocarbon oils, for example those with linear or branched, saturated or unsaturated $C_7$-$C_{40}$-carbon chains, for example Vaseline, dodecane, isododecane, cholesterol, lanolin, synthetic hydrocarbons such as polyolefins, in particular polyisobutene, hydrogenated polyisobutene, polydecane, and also hexadecane, isohexadecane, paraffin oils, isoparaffin oils, e.g. the commercial products of the Permethyl® series, squalane, squalene, and alicyclic hydrocarbons, e.g. the commercial product 1,3-di-(2-ethylhexyl)cyclo-hexane (Cetiol® S), ozocerite, and ceresine.

Likewise of suitability are silicone oils and silicone waxes, preferably dimethylpolysiloxanes and cyclomethicones, polydialkylsiloxanes $R_3SiO(R_2SiO)_xSiR_3$, where R is methyl or ethyl, particularly preferably methyl, and x is a number from 2 to 500, for example the dimethicones available under the trade names VICASIL (General Electric Company), DOW CORNING 200, DOW CORNING 225, DOW CORNING 200 (Dow Corning Corporation), and also the dimethicones available under SilCare® Silicone 41M65, SilCare® Silicone 41M70, SilCare® Silicone 41M80 (Clariant), stearyldimethylpolysiloxane, $C_{20}$-$C_{24}$-alkyldimethylpolysiloxane, $C_{24}$-$C_{28}$-alkyldimethylpolysiloxane, but also the methicones available under SilCare® Silicone 41M40, SilCare® Silicone 41M50 (Clariant), also trimethylsiloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty-acid-, alcohol-, polyether-, epoxy-, fluorine- and/or alkyl-modified silicone compounds, and also polyethersiloxane copolymers.

The compositions according to the invention can comprise, as further auxiliaries and additives, for example waxes, emulsifiers, coemulsifiers, solubilizers, electrolytes, hydroxy acids, stabilizers, cationic polymers, film formers, further thickeners, gelling agents, superfatting agents, refatting agents, antimicrobial active ingredients, biogenetic active ingredients, astringents, deodorizing substances, sun protection filters, antioxidants, humectants, solvents, colorants, pearlizing agents, fragrances, opacifiers and/or silicones.

The compositions according to the invention can comprise waxes, for example paraffin waxes, microwaxes and ozokerite, bees wax and its part fractions, and also bees wax derivatives, waxes from the group of the homopolymeric polyethylenes or copolymers of the α-olefins, and also natural waxes such as rice wax, candellila wax, carnauba wax, Japan wax or shellac wax.

Emulsifiers, coemulsifiers and solubilizers which can be used are nonionic, anionic, cationic or amphoteric surface-active compounds.

Suitable nonionogenic surface-active compounds are preferably: addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally the ethylene oxide addition products thereof; addition products of from 15 to 60 mol of ethylene oxide onto castor oil and/or hydrogenated castor oil; polyol and in particular polyglycerol esters, such as e.g. polyglycerol polyricinoleate and polyglycerol poly-12-hydroxystearate. Ethoxylated fatty amines, fatty acid amides, fatty acid alkanolamides and mixtures of compounds from two or more of these substance classes are likewise preferably suitable.

Suitable ionogenic coemulsifiers are e.g. anionic emulsifiers, such as mono-, di- or triphosphoric acid esters, soaps (e.g. sodium stearate), fatty alcohol sulfates, but also cationic emulsifiers such as mono-, di- and trialkyl quats and polymeric derivatives thereof.

As regards amphoteric emulsifiers, alkylaminoalkylcarboxylic acids, betaines, sulfobetaines and imidazoline derivatives are preferably available.

Particular preference is given to using fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols and cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol(19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol (14) isocetyl ether, polyethylene glycol(15) isocetyl ether, polyethylene glycol(16) isocetyl ether, polyethylene glycol (17) isocetyl ether, polyethylene glycol(18) isocetyl ether, polyethylene glycol(19) isocetyl ether, polyethylene glycol (20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolaurylether, polyethylene glycol(13) cetyl stearyl ether, polyethylene glycol(14) cetyl stearyl ether, polyethylene glycol (15) cetyl stearyl ether, polyethylene glycol(16) cetyl stearyl ether, polyethylene glycol(17) cetyl stearyl ether, polyethylene glycol(18) cetyl stearyl ether, polyethylene glycol(19) cetyl stearyl ether.

Preference is likewise given to fatty acid ethoxylates selected from the group of ethoxylated stearates, isostearates and oleates, in particular polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol (14) oleate, polyethylene glycol(15) oleate, polyethylene glycol(16) oleate, polyethylene glycol(17) oleate, polyethylene glycol(18) oleate, polyethylene glycol(19) oleate, polyethylene glycol(20) oleate.

Sodium laureth-11 carboxylate can advantageously be used as ethoxylated alkylethercarboxylic acid or salts thereof.

Polyethylene glycol(60) evening primrose glycerides can advantageously be used as ethoxylated triglycerides.

It is also advantageous to select the polyethylene glycol glycerol fatty acid esters from the group polyethylene glycol (20) glycerol laurate, polyethylene glycol (6) glyceryl caprate/caprinate, polyethylene glycol(20) glyceryl oleate, polyethylene glycol(20) glyceryl isostearate and polyethylene glycol(18) glyceryl oleate/cocoate.

Among the sorbitan esters, polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate are particularly suitable.

Particularly advantageous coemulsifiers are glycerol monostearate, glycerol monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol(2) stearyl ether (steareth-2), alkylmethicone copolyols and alkyldimethicone copolyols, in particular cetyldimethicone copolyol (ABIL® EM 90), laurylmethicone copolyol or amodimethicone glycerocarbamate (SilCare® Silicone WSI, Clariant).

If the compositions according to the invention comprise one or more substances selected from the group consisting of emulsifiers, coemulsifiers and solubilizers, this one substance or these two or more substances, based on the total weight of the corresponding composition according to the invention, is or are present preferably in an amount of from 0.1 to 20.0% by weight, particularly preferably in an amount of from 0.5 to 10.0% by weight and especially preferably in an amount of from 1.0 to 5.0% by weight, in the compositions according to the invention.

Electrolytes which can be used are inorganic salts, preferably ammonium or metal salts, particularly preferably of halides, for example $CaCl_2$, $MgCl_2$, LiCl, KCl and NaCl, carbonates, hydrogencarbonates, phosphates, sulfates, nitrates, particularly preferably sodium chloride, and/or organic salts, preferably ammonium or metal salts, particularly preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid.

These also include aluminum salts, preferably aluminum chlorhydate or aluminum-zirconium complex salts.

In one preferred embodiment of the invention, the compositions according to the invention therefore comprise one or more substances selected from inorganic and organic salts.

As electrolyte, the compositions according to the invention can also comprise mixtures of different salts.

If the compositions according to the invention comprise one or more electrolytes, these are present, based on the total weight of the corresponding composition according to the invention, preferably in an amount of from 0.01 to 20.0% by weight, particularly preferably in an amount of from 0.1 to 10.0% by weight and especially preferably in an amount of from 0.5 to 5.0% by weight, in the compositions according to the invention.

The polymers according to the invention are acid-stable and are preferably suitable for use in cosmetic, pharmaceutical and/or dermatological compositions with a low pH from 2 to 6, in particular for products for hand and skin disinfection, and also for skincare.

The use of acidic additives and salts thereof sometimes makes it necessary to adjust the pH of the cosmetic or dermatological compositions to a clearly acidic range.

In a further preferred embodiment of the invention, the compositions according to the invention comprise one or more hydroxy acids, particularly preferably one or more substances selected from alpha- and beta-hydroxy acids.

As regards hydroxy acids, the compositions according to the invention can preferably comprise lactic acid, glycolic acid, salicylic acid and alkylated salicylic acids and citric acid. Furthermore, formulations according to the invention can comprise further acidic components. Suitable active ingredients are tartaric acid, mandelic acid, caffeic acid, pyruvic acid, oligooxa mono- and dicarboxylic acids, fumaric acid, retinoic acid, sulfonic acids, benzoic acid, kojic acid, fruit acid, malic acid, gluconic acid, pyruvic acid, galacturonic acid, ribonic acid, and all derivatives thereof, polyglycol diacids in free or partially neutralized form, vitamin C (ascorbic acid), vitamin C derivatives, dihydroxyacetone and skin-whitening actives such as arbutin or glycyrrhetic acid and salts thereof. If the compositions according to the invention comprise one or more of these substances just mentioned, this one substance or these two or more substances is/are present, based on the total weight of the corresponding composition according to the invention, preferably in an amount of from 0.1 to 20.0% by weight, particularly preferably in an amount of from 0.2 to 10.0% by weight and especially preferably in an amount of from 0.5 to 5.0% by weight, in the compositions according to the invention.

In a further preferred embodiment of the invention, the compositions according to the invention therefore comprise one or more substances selected from vitamin C and vitamin C derivatives, the vitamin C derivatives preferably being selected from sodium ascorbyl phosphate, magnesium ascorbyl phosphate and magnesium ascorbyl glucoside.

In a further preferred embodiment of the invention, the compositions according to the invention comprise one or more substances selected from benzoic acid, sorbic acid, salicylic acid, lactic acid and paramethoxybenzoic acid. As a result of the fact that the polymers according to the invention also thicken in the acidic pH range and build up a yield point, it is possible to work with the aforementioned organic acids as preservatives.

In addition to the polymers according to the invention, additional stabilizers which can be used are metal salts of fatty acids, such as e.g. magnesium stearate, aluminum stearate and/or zinc stearate. If the compositions according to the invention comprise one or more of these substances just mentioned, this one substance or these two or more substances is/are, based on the total weight of the corresponding composition according to the invention, present preferably in an amount of from 0.1 to 10.0% by weight, particularly preferably in an amount of from 0.5 to 8.0% by weight and especially preferably in an amount of from 1.0 to 5.0% by weight, in the compositions according to the invention.

Suitable cationic polymers are the substances known under the INCI name "Polyquaternium", in particular Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG tridecheth (Salcare SC95), PVP-dimethylaminoethylmethacrylate copolymer, guar hydroxypropyltriammonium chloride, and also calcium alginate and ammonium alginate. Furthermore, it is possible to use cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as e.g. amidomethicones; copolymers of adipic acid and dimethylaminohydroxypropyldiethylenetriamine; polyaminopolyamide and cationic chitin derivatives, such as, for example, chitosan.

If the compositions according to the invention comprise one or more of the aforementioned cationic polymers, these are present, based on the total weight of the corresponding composition according to the invention, preferably in an amount of from 0.1 to 5.0% by weight, particularly preferably in an amount of from 0.2 to 3.0% by weight and especially preferably in an amount of from 0.5 to 2.0% by weight, in the compositions according to the invention.

Furthermore, the compositions according to the invention can comprise film formers, which are selected, depending on the intended use, from salts of phenylbenzimidazolesulfonic acid, water-soluble polyurethanes, for example $C_{10}$-polycarbamyl polyglyceryl ester, polyvinyl alcohol, polyvinylpyrrolidone copolymers, for example vinylpyrrolidone/vinyl acetate copolymer or PVP/eicosene copolymers, maleated polypropylene polymers, water-soluble acrylic acid polymers/copolymers or esters or salts thereof, for example partial ester copolymers of acrylic/methacrylic acid, water-soluble cellulose, for example hydroxymethylcellulose, hydroxyethylcellulose, hydroxypropylcellulose, water-soluble quaternium, polyquaternium, carboxyvinyl polymers, such as carbomers and salts thereof, polysaccharides, for example polydextrose and glucan, vinyl acetate/crotonate, available for example under the trade name Aristoflex® A 60 (Clariant).

If the compositions according to the invention comprise one or more film formers, these are present, based on the total weight of the corresponding composition according to the invention, preferably in an amount of from 0.1 to 10.0% by weight, particularly preferably in an amount of from 0.2 to 5.0% by weight and especially preferably in an amount of from 0.5 to 3.0% by weight, in the compositions according to the invention.

The desired viscosity of the compositions can be established by adding further thickeners and gelling agents. Of suitability are preferably cellulose ethers and other cellulose derivatives (e.g. carboxymethylcellulose, hydroxyethylcellulose), gelatin, starch and starch derivatives, sodium alginates, fatty acid polyethylene glycol esters, agar agar, carrageenan, traganth or dextrin derivatives, in particular dextrin esters. Also of suitability are metal salts of fatty acids, preferably having 12 to 22 carbon atoms, for example sodium stearate, sodium palmitate, sodium laurate, sodium arachidate, sodium behenate, potassium stearate, potassium palmitate, sodium myristate, aluminum monostearate, hydroxy fatty acids, for example 12-hydroxystearic acid, 16-hydroxyhexadecanoyl acid; fatty acid amides; fatty acid allkanolamides; dibenzalsorbitol and alcohol-soluble poly-amides and polyacrylamides or mixtures thereof. Furthermore, crosslinked and uncrosslinked polyacrylates such as carbomer, sodium polyacrylates or sulfonic-acid-containing polymers such as ammonium acryloyldimethyltaurateNP copolymer or sodium acryloyldimethyltaurate/VP copolymer can be used.

If the compositions according to the invention comprise one or more substances selected from the group consisting of thickeners and gelling agents, this one substance or these two or more substances is/are present, based on the total weight of the corresponding composition according to the invention, preferably in an amount of from 0.01 to 20.0% by weight, particularly preferably in an amount of from 0.1 to 10.0% by weight, especially preferably in an amount of from 0.2 to 3.0% by weight and extraordinarily preferably in an amount of from 0.4 to 2.0% by weight, in the compositions according to the invention.

Superfatting agents or refatting agents which can be used are preferably lanolin and lecithin, nonethoxylated and polyethoxylated or acylated lanolin and lecithin derivatives, polyol fatty acid esters such as glyceryl oleate, mono-, di- and triglycerides and/or fatty acid alkanolamides, the latter simultaneously serving as foam stabilizers. If the compositions according to the invention comprise one or more of the substances just stated, this one substance or these two or more substances are present, based on the total weight of the corresponding composition according to the invention, preferably in an amount of from 0.01 to 10.0% by weight, particularly preferably in an amount of from 0.1 to 5.0% by weight and especially preferably in an amount of from 0.5 to 3.0% by weight, in the compositions according to the invention.

In a further preferred embodiment of the invention, the compositions according to the invention comprise one or more antimicrobial active ingredients and are preferably in the form of disinfection compositions and particularly preferably in the form of disinfection gels.

As regards antimicrobial active ingredients, it is possible to use cetyltrimethylammonium chloride, cetylpyridinium chloride, benzethonium chloride, diisobutylethoxyethyldimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysinehexadecylamide, citrate heavy metal salts, salicylates, piroctose, in particular zinc salts, pyrithiones and heavy metal salts thereof, in particular zinc pyrithione, zinc phenolsulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and Octopirox®, iodopropynyl butylcarbamate, methylchloroisothiazolinone, methylisothiazolinone, methyldibromoglutaronitrile, AgCl, chloroxylenol, Na salt of diethylhexylsulfosuccinate, sodium benzoate, and also phenoxyethanol, benzyl alcohol, phenoxyisopropanol, parabens, preferably butylparaben, ethylparaben, methylparaben and propylparaben, and Na salts thereof, pentanediol 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethylglycinate, hydroxyethylglycine of sorbic acid and combinations of these active substances.

If the compositions according to the invention comprise one or more antimicrobial active ingredients, these are present, based on the total weight of the corresponding composition according to the invention, preferably in an amount of from 0.001 to 5.0% by weight, particularly preferably in an amount of from 0.01 to 3.0% by weight and especially preferably in an amount of from 0.1 to 2.0% by weight, in the compositions according to the invention.

The compositions according to the invention can furthermore comprise biogenic active ingredients selected from plant extracts, such as, for example, Aloe Vera, and also local anesthetics, antibiotics, antiphlogistics, antiallergics, corticosteroids, sebostatics, Bisabolol®, allantoin, Phytantriol®, proteins, vitamins selected from niacin, biotin, vitamin B2, vitamin B3, vitamin B6, vitamin B3 derivatives (salts, acids, esters, amides, alcohols), vitamin C and vitamin D derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, and also vitamin E and/or derivatives thereof.

If the compositions according to the invention comprise one or more biogenic active ingredients, these are present, based on the total weight of the corresponding composition according to the invention, preferably in an amount of from 0.001 to 5.0% by weight, particularly preferably in an amount of from 0.01 to 3.0% by weight and especially preferably in an amount of from 0.1 to 2.0% by weight, in the compositions according to the invention.

The compositions according to the invention can comprise astringents, preferably magnesium oxide, aluminum oxide, titanium dioxide, zirconium dioxide and zinc oxide, oxide hydrates, preferably aluminum oxide hydrate (Boehmite) and hydroxides, preferably of calcium, magnesium, aluminum, titanium, zirconium or zinc, and also aluminum chlorohydrates. If the compositions according to the invention comprise one or more astringents, these are present, based on the total weight of the corresponding composition according to the invention, preferably in an amount of from 0.001 to 50.0% by weight, particularly preferably in an amount of from 0.01 to 10.0% by weight and especially preferably in an amount of from 0.1 to 10.0% by weight, in the compositions according to the invention.

The deodorizing substances are preferably allantoin and bisabolol. If the compositions according to the invention comprise one or more deodorizing substances, these are present, based on the total weight of the corresponding composition according to the invention, preferably in an amount of from 0.0001 to 10.0% by weight, in the compositions according to the invention.

In a further preferred embodiment of the invention, the compositions according to the invention comprise one or more substances selected from inorganic and organic UV filters and are particularly preferably in the form of sunscreen compositions.

The compositions according to the invention can comprise, as pigments/micropigments and also as inorganic sun protection filters or UV filters, microfine titanium dioxide, mica-titanium oxide, iron oxides, mica-iron oxide, zinc oxide, silicon oxides, ultramarine blue or chromium oxides.

The organic sun protection filters and UV filters are preferably selected from 4-aminobenzoic acid, 3-(4'-trimethylammonium)benzylideneboran-2-one methylsulfate, camphor benzalkoniummethosulfate, 3,3,5-trimethylcyclohexylsalicylate, 2-hydroxy-4-methoxybenzophenone, 2-phenylbenzimidazole-5-sulfonic acid and its potassium, sodium and triethanolamine salts, 3,3'-(1,4-phenylenedimethine)bis(7,7-dimethyl-2-oxobicyclo[2.2.1]heptane-1-methanesulfonic acid) and its salts, 1-(4-tert-butylphenyl)-3-(4-methoxyphenyl)propane-1,3-dione, 344% sulfo) benzylidenebornan-2-one and its salts, 2-ethylhexyl 2-cyano-3,3-diphenylacrylate, polymers of N-[2(and 4)-(2-oxoborn-3-ylidenemethyl)benzyl]acrylamide, 2-ethylhexyl, 4-methoxycinnamate, ethoxylated ethyl 4-aminobenzoate, isoamyl 4-methoxycinnamate, 2,4,6-tris-[p-(2-ethylhexyloxycarbonyl)anilino]-1,3,5-triazine, 2-(2H-benzotriazol-2-yl)-4-methyl-6-(2-methyl-3-(1,3,3,3-tetramethyl-1-(trimethylsilyloxy)disiloxanyl)propyl)phenol, bis(2-ethylhexyl) 4,4'-[(6-[4-((1,1-dimethylethyl)aminocarbonyl)phenylamino]-1,3,5-triazin-2,4-yl)diimino]bisbenzoate, benzophenone-3, benzophenone-4 (acid), 3-(4'-methylbenzylidene)-D,L-camphor, 3-benzylidenecamphor, 2-ethylhexyl salicylate, 2-ethylhexyl 4-dimethylamino benzoate, hydroxy-4-methoxybenzophenone-5-sulfonic acid (sulfisobenzonum) and the sodium salt, 4-isopropylbenzyl salicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium and triethanolamine salts, octylmethoxycinnamic acid, isopentyl-4-methoxycinnamic acid, isoamyl-p-methoxycinnamic acid, 2,4,6-trianilino(p-carbo-2'-ethylhexyl-1'-oxy)-1,3,5-triazine (octyltriazone) phenol, 2-2(2H-benzotriazol-2-yl)-4-methyl-6-(2-methyl-3-(1,3,3,3-tetramethyl-1-(trimethylsilyl)oxy)disiloxanyl)propyl (drometrizole trisiloxane)benzoic acid, 4,4-((6-(((1,1-dimethylethyl)amino)carbonyl)phenyl)amino)-1,3,5-triazine-2,4-diyl)diimino)bis,bis(2-ethylhexyl)ester)benzoic acid, 4,4-((6-(((1,1-dimethylethyl)amino)carbonyl)phenyl)amino)-1,3,5-triazine-2,4-diyl)diimino)bis,bis(2-ethylhexyl)ester), 3-(4'-methylbenzylidene)-D,L-camphor (4-methylbenzylidenecamphor), benzylidenecamphorsulfonic acid, octocrylene, polyacrylamidomethylbenzylidenecamphor, 2-ethylhexyl salicylate (octyl salicylate), 2-ethylhexyl 4-dimethylaminobenzoate (octyl dimethyl PABA), PEG-25 PABA, 2-hydroxy-4-methoxybenzophenone-5-sulfonic acid (benzophenone-5) and the Na salt, 2,2'-methylenebis-6-(2H-benzotriazol-2-yl)-4-(tetramethylbutyl)-1,1,3, 3-phenol, sodium salt of 2-2'-bis(1,4-phenylene)-1H-benzimidazole-4,6-disulfonic acid, (1,3,5)-triazine-2,4-bis ((4-(2-ethylhexyloxy)-2-hydroxy)phenyl)-6-(4-methoxyphenyl), 2-ethylhexyl 2-cyano-3,3-diphenyl-2-propenoate, glyceryl octanoate, di-p-methoxycinnamic acid, p-aminobenzoic acid and esters thereof, 4-tert-butyl-4'-methoxydibenzoylmethane, 4-(2-β-glucopyranoxy) propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl dimethoxybenzylidenedioxoimidazolidinepropionate, methylenebisbenztriazolyl tetramethylbutylphenol, phenyldibenzimidazol tetrasulfonate, bis-ethylhexyloxyphenol methoxyphenoltriazine, tetrahydroxybenzophenones, terephthalylidenedicamphorsulfonic acid, 2,4,6-tris[4,2-ethylhexyloxycarbonyl)anilino]-1,3,5-triazine, methylbis(trimethylsiloxy)silylisopentyltrimethoxycinnamic acid, amyl p-dimethylanninobenzoate, amyl p-dimethylaminobenzoate, 2-ethylhexyl p-dimethylanninobenzoate, isopropyl p-methoxycinnamic acid/diisopropylcinnamic acid ester, 2-ethylhexyl-p-methoxycinnamic acid, 2-hydroxy-4-methoxybenzophenone, 2-hydroxy-4-methoxybenzophenone-5-sulfonic acid and the trihydrate, and 2-hydroxy-4-methoxybenzophenone-5-sulfonate sodium salt and phenylbenzimidazole sulfonic acid.

If the compositions according to the invention comprise one or more sun protection filters, these are present, based on the total weight of the corresponding composition according to the invention, preferably in an amount of from 0.001 to 30.0% by weight, particularly preferably in an amount of from 0.05 to 20.0% by weight and especially preferably in an amount of from 1.0 to 10.0% by weight, in the compositions according to the invention.

The compositions according to the invention can comprise one or more antioxidants, preferably selected from amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoids, carotenes (e.g. α-carotene, 3-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and also salts thereof, dilauryl thiodipropionate, distearyl thiodipropionate, thiodipropionoic acid and derivatives thereof (e.g. esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses, also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubichinon and ubichinol and derivatives thereof, vitamin C and derivatives (e.g. ascorbyl palmitate, Mg ascorbyl phosphate, ascorbyl acetate), tocopherols and derivates (e.g. vitamin E acetate), vitamin A and derivatives (vitamin A palmitate), and also coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), superoxide dismutase and the derivatives suitable according to the invention (salts, esters, ethers, sugars, nucleotides, nucleosides, peptides and lipids) of these specified substances.

The antioxidants can protect the skin and the hair against oxidative stress. Preferred antioxidants here are vitamin A and derivatives thereof, and vitamin A and derivatives thereof.

If the compositions according to the invention comprise one or more antioxidants, these are present in the compositions according to the invention preferably in an amount of from 0.001 to 30.0% by weight, particularly preferably in an amount of from 0.05 to 20.0% by weight and especially preferably in an amount of from 1.0 to 10.0% by weight, based on the total weight of the corresponding composition according to the invention.

Furthermore, humectants selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxyethylurea, hydroxy acids, panthenol and derivatives thereof, for example D-panthenol (R-2,4-dihydroxy-N-(3-hydroxypropyl)-3,3-dimethylbutamide), D,L-panthenol, calcium pantothenate, panthetin, pantothein, panthenyl ethyl ether, isopropyl palmitate, glycerol and/or sorbitol can be used. If the compositions according to the invention comprise one or more humectants, these are present in the compositions according to the invention preferably in an amount of from 0.1 to 15.0% by weight and particularly preferably in an amount of from 0.5 to 5.0% by weight, based on the total weight of the corresponding composition according to the invention.

Additionally, the compositions according to the invention can comprise organic solvents. In principle, suitable organic solvents are all mono- or polyhydric alcohols. Preference is given to using alcohols having 1 to 4 carbon atoms such as ethanol, propanol, isopropanol, n-butanol, isobutanol, tert-butanol, glycerol and mixtures of the specified alcohols. Further preferred alcohols are polyethylene glycols with a relative molecular mass below 2000. In particular, preference is given to using polyethylene glycol with a relative molecular mass between 200 and 600 and in amounts up to 45.0% by weight and polyethylene glycol with a relative molecular mass between 400 and 600 in amounts of from 5.0 to 25.0% by weight. Further suitable solvents are, for example, triacetin (glycerol triacetate) and 1-methoxy-2-propanol.

The compositions according to the invention can comprise one or more substances selected from colorants, e.g. dyes and/or pigments. The dyes and/or pigments present in the formulations according to the invention, either organic or inorganic dyes and pigments, are selected from the corresponding positive list of the Cosmetics Ordnance or the EC List of cosmetic colorants.

| Chemical or other name | CIN | Color |
| --- | --- | --- |
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfonic acid diethylamide-1'-phenylazo)-3-hydroxy-5"-chloro-2",4"-dimethoxy-2-naphthoic acid anilide | 12490 | red |
| Disperse Yellow 16 | 12700 | yellow |
| 1-(4-Sulfo-1-phenylazo)-4-aminobenzenesulfonic acid | 13015 | yellow |
| 2,4-Dihydroxyazobenzene-4'-sulfonic acid | 14270 | orange |
| 2-(2,4-Dimethylphenylazo-5-sulfonic acid)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonic acid-4-chloro-5-carboxylic acid-1-phenylazo)-2-hydroxynaphthalene | 15525 | red |
| 1-(3-Methylphenylazo-4-sulfonic acid)-2-hydroxynaphthalene | 15580 | red |
| 1-(4',(8')-Sulfonic acid naphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxypyrazolone-3-carboxylic acid | 19140 | yellow |
| Pigment Yellow 16 | 20040 | yellow |
| 2,6-(4'-Sulfo-2",4"-dimethyl)bisphenylazo-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4"-Sulfo-1"'-phenylazo)-7'-sulfo-1'-naphthylazo]-1-hydroxy-7-aminonaphthalene-3,6-disulfonic acid | 27755 | black |
| 4'-[(4"-Sulfo-1"'-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-Carotenealdehyde ($C_{30}$) | 40820 | orange |
| trans-Apo-8'-Carotenic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4"-bis(diethylamino)triphenyl-carbinol | 42051 | blue |
| 4-[(4-N-Ethyl-p-sulfobenzylamino)phenyl-(4-hydroxy-2-sulfophenyl)(methylene)-1-(N-ethyl-N-p-sulfobenzyl)-2,5-cyclohexadieneimine] | 42053 | green |
| Acid Blue 7 | 42080 | blue |
| (N-Ethyl-p-sulfobenzylaminophenyl-(2-sulfophenyl)-methylene-(N-ethyl-N-p-sulfobenzyl) cyclohexadieneimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4"-(N-diethyl)-amino-2-methyl-N-ethyl-N-m-sulfobenzylfuchsonimmonium | 42735 | blue |
| 4'-(N-Dimethyl)amino-4"-(N-phenyl)aminonaphtho-N-dimethylfuchsonimmonium | 44045 | blue |
| 2-Hydroxy-3,6-disulfo-4,4'-bisdimethylaminonaphtho-fuchsinimmonium | 44090 | green |
| Acid red | 45100 | red |

-continued

| Chemical or other name | CIN | Color |
|---|---|---|
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidine)anthraquinone | 61570 | green |
| Acid Blue 80 | 61585 | blue |
| Acid Blue 62 | 62045 | blue |
| N,N'-Dihydro-1,2,1',2'-anthraquinoneazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Natural Yellow 6,19; Natural Red 1 | 75100 | yellow |
| Bixin, Nor-Bixin | 75120 | orange |
| Lycopene | 75125 | yellow |
| trans-alpha, beta- or gamma-Carotene | 75130 | orange |
| Keto- and/or hydroxyl derivatives of carotene | 75135 | yellow |
| Guanine or pearlescent agents | 75170 | white |
| 1,7-Bis(4-hydroxy-3-methoxyphenyl)-1,6-heptadiene-3,5-dione | 75300 | yellow |
| Complex salt (Na,Al,Ca) of carminic acid | 75470 | red |
| Chlorophyll a and b; copper compounds of the chlorophylls and chlorophyllines | 75810 | green |
| Aluminum | 77000 | white |
| Alumina hydrate | 77002 | white |
| Water-containing aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromic oxide | 77288 | green |
| Chromic oxide, water-containing | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxides and hydroxides | 77491 | red |
| Hydrated iron oxide | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Caramel | | brown |
| Capsanthin, Capsorubin | | orange |
| Betanine | | red |
| Benzopyrilium salts, anthocyanines | | red |
| Aluminum, zinc, magnesium and calcium stearate | | white |
| Bromothymol Blue | | blue |
| Bromocresol Green | | green |
| Acid Red 195 | | red |

Also advantageous are oil-soluble natural dyes, such as e.g. paprika extracts, β-carotene and cochineal.

Pearlescent pigments are also advantageously used, e.g. pearl essence (guanine/hypoxanthine mixed crystals from fish scales) and mother-of-pearl (ground mussel shells), monocrystalline pearlescent pigments such as e.g. bismuth oxychloride (BiOCl), layer-substrate pigments, e.g. mica/metal oxide, silver-white pearlescent pigments of $TiO_2$, interference pigments ($TiO_2$, varying layer thickness), color luster pigments ($Fe_2O_3$) and combination pigments ($TiO_2/Fe_2O_3$, $TiO_2/Cr_2O_3$, $TiO_2$/Prussian blue, $TiO_2$/carmine).

Within the context of the present invention, effect pigments are to be understood as meaning pigments which bring about particular optical effects as a result of their refractive properties. Effect pigments impart luster or glitter effects to the treated surface (skin, hair, mucosa) or are able to optically conceal skin unevennesses and skin wrinkles by means of diffuse light scattering. As a particular embodiment of the effect pigments, interference pigments are preferred. Particularly suitable effect pigments are, for example, mica particles which are coated with at least one metal oxide. Besides mica, a sheet silicate, silica gel and other $SiO_2$ modifications are also suitable as carriers. A metal oxide which is often used for the coating is, for example, titanium oxide, to which, if desired, iron oxide can be admixed. The reflection properties can be influenced via the size and the shape (e.g. spherical, ellipsoidal, flattened, planar, nonplanar) of the pigment particles and also via the thickness of the oxide coating. Other metal oxides too, e.g. bismuth oxychloride (BiOCl), and the oxides of, for example, titanium, in particular the $TiO_2$ modifications anatase and rutile, and of aluminum, tantalum, niobium, zirconium and hafnium. Magnesium fluoride ($MgF_2$) and calcium fluoride (fluorspar, $CaF_2$) can also be used to produce effect pigments.

The effects can be controlled not only via the particle size but also via the particle size distribution of the pigment assembly. Suitable particle size distributions range e.g. from 2-50 μm, 5-25 μm, 5-40 μm, 5-60 μm, 5-95 μm, 5-100 μm, 10-60 μm, 10-100 μm, 10-125 μm, 20-100 μm, 20-150 and <15 μm. A broader particle size distribution, e.g. of 20-150 brings about glittering effects, whereas a narrower particle size distribution of <15 μm provides a uniform satin appearance.

If the compositions according to the invention comprise one or more effect pigments, these are present in the compositions according to the invention preferably in an amount of from 0.1 to 20.0% by weight, particularly preferably in an amount of from 0.5 to 10.0% by weight and especially preferably in an amount of from 1.0 to 5.0% by weight, based on the total weight of the corresponding composition according to the invention.

Preferably suitable as pearlizing component are fatty acid monoalkanolamides, fatty acid dialkanolamides, monoesters or diesters of alkylene glycols, in particular ethylene glycol and/or propylene glycol or oligomers thereof, with higher fatty acids, such as e.g. palmitic acid, stearic acid and behenic acid, monoesters or polyesters of glycerol with carboxylic acids, fatty acids and metal salts thereof, ketosulfones or mixtures of the specified compounds.

Particular preference is given to ethylene glycol distearates and/or polyethylene glycol distearates having on average 3 glycol units.

If the compositions according to the invention comprise one or more pearlizing compounds, these are preferably present in the compositions according to the invention in an amount of from 0.1 to 15.0% by weight and particularly preferably in an amount of from 1.0 to 10.0% by weight, based on the total weight of the corresponding composition according to the invention.

Fragrance or perfume oils which may be used are individual odorant compounds, e.g. the synthetic products of the ester, ether, aldehyde, ketone, alcohol and hydrocarbon types. Odorant compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ether, the aldehydes include e.g. the linear alkanals having 8 to 18 carbon atoms, citral, citronellal, citronellyloxyacetaldehyde, cyclamenaldehyde, hydroxycitronellal, lilial and bourgeonal, the ketones include e.g. the ionones, alpha-isomethylionone and methyl cedryl ketone, the alcohols include anethol, citronellol, eugenol, geraniol, linalool, phenylethyl alcohol and terpineol, the hydrocarbons include primarily the terpenes and balsams. Preference is given to using mixtures of different odorants which together produce a pleasing scent note.

Perfume oils can also comprise natural odorant mixtures, as are accessible from vegetable or animal sources, e.g. pine oil, citrus oil, jasmine oil, lily oil, rose oil or ylang ylang oil. Essential oils of relatively low volatility, which are mostly used as aroma components, are also suitable as perfume oils, e.g. sage oil, chamomile oil, clove oil, Melissa oil, mint oil, cinnamon leaf oil, linden blossom oil, juniper berry oil, vetiver oil, olibanum oil, galbanum oil and ladanum oil.

Opacifiers which can be used are polymer dispersions, in particular polyacrylate derivative dispersions, polyacrylamide derivative dispersions, poly(acrylate derivative-co-acrylamide derivate) dispersions, poly(styrene derivatives-co-acrylate derivative) dispersions, saturated and unsaturated fatty alcohols.

As regards silicones, the substances specified above under the silicone oils and silicone waxes can be used.

Acids or alkalis which can be used to adjust the pH are preferably mineral acids, in particular HCl, inorganic bases, in particular NaOH or KOH, and organic acids, in particular citric acid.

The compositions according to the invention have pH values of preferably 2 to 10, particularly preferably from 2 to 7 and especially preferably from 2.5 to 6.5.

The polymers according to the invention are advantageously suitable as thickener, consistency regulator, emulsifier, sensory additive, solubilizer, dispersant, lubricant, adhesive, stabilizer or yield-point former.

The invention therefore further provides the use of one or more of the polymers according to the invention as thickener, consistency regulator, emulsifier, sensory additive, solubilizer, dispersant, lubricant, adhesive, stabilizer or yield-point former, preferably as thickener, consistency regulator or sensory additive, particularly preferably as thickener or sensory additive and especially preferably as sensory additive, extraordinarily preferably in cosmetic, dermatological or pharmaceutical compositions.

In a further preferred embodiment of the invention, the polymers according to the invention are used for stabilizing emulsions, preferably salt-containing emulsions and particularly preferably salt-containing cosmetic, dermatological or pharmaceutical emulsions.

The polymers according to the invention are acid-stable and are advantageously suitable for use in cosmetic, dermatological or pharmaceutical compositions with a low pH, in particular for the care and treatment of the body skin or facial skin.

The present invention therefore further provides the use of one or more polymers according to the invention for the care and treatment of the body skin or facial skin, preferably in cosmetic, dermatological or pharmaceutical compositions, particularly preferably in acidic cosmetic, dermatological or pharmaceutical compositions.

It is also advantageous that the polymers according to the invention can also be used without co-use of an additional sensory additive and/or without co-use of an additional thickener in compositions, preferably in cosmetic, dermatological or pharmaceutical compositions. The co-use of additional sensory additives and/or thickeners is therefore not obligatory, but possible. A combination with other known sensory additives and/or thickeners may be desirable for the purposes of establishing special cosmetic profiles and for utilizing synergistic effects. Preferably, these compositions are present as aqueous, aqueous-alcoholic, aqueous-surfactant-containing, aqueous-alcoholic surfactant-containing cosmetic, dermatological or pharmaceutical compositions, in which case they preferably do not comprise any additional substance selected from sensory additives and additional thickeners.

As already mentioned, the compositions according to the invention comprise, in a further preferred embodiment of the invention, one or more substances selected from inorganic and organic UV filters and are particularly preferably present in the form of sunscreen compositions. The polymers according to the invention have the advantage here that they are able to increase the sun protection factor of the sunscreen compositions.

The present invention therefore also provides the use of one or more of the polymers according to the invention for increasing the sun protection factor of sunscreen compositions.

The examples and applications below serve to explain the invention in more detail without, however, limiting it thereto.

A) Examples Relating to the Preparation of Polymers According to the Invention

General polymerization procedure for preparing the polymers according to the invention by the precipitation method in tert-butanol 400 g of tert-butanol are introduced as initial charge in a 1 liter quickfit flask with reflux condenser, gas line, internal thermometer and stirrer and admixed with the calculated amount of 2-acrylamido-2-methylpropanesulfonic acid (AMPS®, Lubrizol). Then, the mixture is neutralized by introducing $NH_3$ (desired pH 6-7) and the calculated amount of crosslinker and the calculated amounts of the other comonomers are added to the reaction mixture. Should the pH of the reaction mixture after adding the comonomers have drifted into the acidic range, it is neutralized again by introducing $NH_3$ (desired pH 6-7). After rendering the mixture inert with $N_2$ or argon, dilauroyl peroxide (DLP) or dimethyl 2,2'-azobis(2-methylpropionate) (V601) is added as initiator at an internal temperature of 60° C. and the polymerization reaction is started. After a few minutes, the finished polymer precipitates out. The mixture is heated at reflux for 2 hours and the polymer is then freed from solvent via a suction filter and dried in vacuo. This procedure can be applied in general to all polymerization reactions described below.

To prepare the polymers of the following examples 1-50, the procedure was in accordance with the general polymerization procedure given above. In the tables listed under examples 1-50 below, the top lines in each case give the absolute amounts of the monomers used for the polymerization and of the initiator (in grams "g"), and the middle line in each case gives the corresponding amounts converted to % by weight. The bottom line in each case gives the molar fraction of the monomers (in mol %) without taking into consideration the initiator.

The abbreviations for the monomers, crosslinkers and initiator given in the examples have the following meaning:
AMP5=2-Acrylamido-2-methylpropanesulfonic acid
HEEA=Hydroxyethylacrylamide
DMAAm=Dimethylacrylamide
NIPA=Isopropylacrylamide
NVP=N-vinylpyrrolidone
MAA=Methacrylic acid
GPTA=Glycerol propoxylate triacrylate
$GP_{15}TA$=Glycerol propoxylate triacrylate (15/3 PO/OH)
TMPTA-PO-3=Trimethylolpropane propoxytriacrylate (3/3 PO/OH)
TMPTA-EO-3=Trimethylolpropane ethoxytriacrylate (3/3 EO/OH)
TMPTA-EO-15=Trimethylolpropane ethoxytriacrylate (15/3 EO/OH)
V601=Dimethyl 2,2'-azobis(2-methylpropionate)
DLP=Dilauroyl peroxide

EXAMPLE 1

| Amount | AMP5 | DMAAm | GPTA | V601 |
|---|---|---|---|---|
| g | 100.0 | 8.50 | 2.08 | 1.4 |
| % by wt. | 89.3 | 7.5 | 1.9 | 1.3 |
| mol % | 84.15 | 15.0 | 0.85 | — |

EXAMPLE 2

| Amount | AMP5 | DMAAm | GPTA | V601 |
|---|---|---|---|---|
| g | 100.0 | 12.10 | 2.22 | 1.4 |
| % by wt. | 86.4 | 10.5 | 1.9 | 1.2 |
| mol % | 79.15 | 20.0 | 0.85 | — |

EXAMPLE 3

| Amount | AMP5 | DMAAm | GPTA | V601 |
|---|---|---|---|---|
| g | 100.0 | 16.10 | 2.37 | 1.4 |
| % by wt. | 83.4 | 13.4 | 2.0 | 1.2 |
| mol % | 74.15 | 25.0 | 0.85 | — |

EXAMPLE 4

| Amount | AMP5 | HEEA | GP15TA | V601 |
|---|---|---|---|---|
| g | 100.00 | 6.20 | 0.90 | 1.90 |
| % by wt. | 91.7 | 5.7 | 0.9 | 1.7 |
| mol % | 89.75 | 10.0 | 0.25 | — |

EXAMPLE 5

| Amount | AMP5 | HEEA | GP15TA | V601 |
|---|---|---|---|---|
| g | 100.00 | 9.85 | 1.90 | 2.00 |
| % by wt. | 87.9 | 8.7 | 1.7 | 1.8 |
| mol % | 84.5 | 15.0 | 0.50 | — |

EXAMPLE 6

| Amount | AMP5 | HEEA | GP15TA | V601 |
|---|---|---|---|---|
| g | 100.00 | 14.10 | 4.02 | 2.20 |
| % by wt. | 83.1 | 11.7 | 3.3 | 1.8 |
| mol % | 79.0 | 20.0 | 1.00 | — |

EXAMPLE 7

| Amount | AMP5 | HEEA | GP15TA | V601 |
|---|---|---|---|---|
| g | 80.00 | 15.20 | 6.97 | 1.80 |
| % by wt. | 76.9 | 14.7 | 6.7 | 1.7 |
| mol % | 73.0 | 25.0 | 2.00 | — |

EXAMPLE 8

| Amount | AMP5 | NIPA | TMPTA-PO-3 | DLP |
|---|---|---|---|---|
| g | 100.00 | 13.80 | 2.88 | 2.40 |
| % by wt. | 84.0 | 11.6 | 2.4 | 2.0 |
| mol % | 79.0 | 20.0 | 1.00 | — |

EXAMPLE 9

| Amount | AMP5 | NIPA | TMPTA-EO-3 | DLP |
|---|---|---|---|---|
| g | 100.00 | 13.80 | 2.60 | 2.40 |
| % by wt. | 84.2 | 11.6 | 2.2 | 2.0 |
| mol % | 79.0 | 20.0 | 1.00 | — |

EXAMPLE 10

| Amount | AMP5 | NIPA | TMPTA-EO-15 | DLP |
|---|---|---|---|---|
| g | 80.00 | 11.05 | 4.65 | 2.00 |
| % by wt. | 81.9 | 11.3 | 4.8 | 2.0 |
| mol % | 79.0 | 20.0 | 1.00 | — |

EXAMPLE 11

| Amount | AMP5 | DMAAm | HEEA | GPTA | V601 |
|---|---|---|---|---|---|
| g | 100.00 | 6.05 | 7.05 | 1.95 | 2.10 |
| % by wt. | 85.4 | 5.2 | 6.0 | 1.7 | 1.7 |
| mol % | 79.2 | 10.0 | 10.05 | 0.75 | — |

EXAMPLE 12

| Amount | AMP5 | DMAAm | HEEA | GPTA | V601 |
|---|---|---|---|---|---|
| g | 100.00 | 3.20 | 14.95 | 3.50 | 2.30 |
| % by wt. | 80.7 | 2.6 | 12.1 | 2.7 | 1.9 |
| mol % | 73.9 | 4.9 | 19.9 | 1.3 | — |

EXAMPLE 13

| Amount | AMP5 | DMAAm | HEEA | GP15TA | V601 |
|---|---|---|---|---|---|
| g | 100.00 | 12.80 | 3.70 | 1.05 | 2.30 |
| % by wt. | 83.4 | 10.7 | 3.1 | 0.9 | 1.9 |
| mol % | 74.75 | 20.0 | 5.0 | 0.25 | — |

EXAMPLE 14

| Amount | AMP5 | DMAAm | HEEA | GP15TA | V601 |
|---|---|---|---|---|---|
| g | 100.00 | 9.75 | 7.58 | 6.49 | 2.30 |
| % by wt. | 79.3 | 7.7 | 6.0 | 5.2 | 1.8 |
| mol % | 73.5 | 15.0 | 10.0 | 1.50 | — |

EXAMPLE 15

| Amount | AMP5 | DMAAm | NVP | GPTA | V601 |
|---|---|---|---|---|---|
| g | 100.00 | 12.60 | 1.75 | 2.29 | 1.20 |
| % by wt. | 84.9 | 10.7 | 1.5 | 1.9 | 1.9 |
| mol % | 76.5 | 20.15 | 2.50 | 0.85 | — |

EXAMPLE 16

| Amount | AMP5 | DMAAm | NVP | GPTA | V601 |
|---|---|---|---|---|---|
| g | 100.00 | 13.00 | 3.65 | 2.36 | 1.20 |
| % by wt. | 83.2 | 10.8 | 3.0 | 2.0 | 1.0 |
| mol % | 74.0 | 20.1 | 5.05 | 0.85 | — |

EXAMPLE 17

| Amount | AMP5 | DMAAm | NVP | GPTA | V601 |
|---|---|---|---|---|---|
| g | 100.00 | 13.95 | 5.70 | 2.54 | 1.30 |
| % by wt. | 81.0 | 11.3 | 4.6 | 2.1 | 1.1 |
| mol % | 70.9 | 20.7 | 7.53 | 0.87 | — |

EXAMPLE 18

| Amount | AMP5 | DMAAm | HEEA | NVP | GPTA | DLP |
|---|---|---|---|---|---|---|
| g | 100.00 | 9.39 | 3.63 | 1.75 | 2.29 | 2.50 |
| % by wt. | 83.6 | 7.9 | 3.0 | 1.5 | 1.9 | 2.1 |
| mol % | 76.55 | 15.1 | 5.0 | 2.50 | 0.85 | — |

EXAMPLE 19

| Amount | AMP5 | DMAAm | HEEA | NVP | TMPTA-PO-3 | DLP |
|---|---|---|---|---|---|---|
| g | 100.00 | 3.00 | 3.51 | 6.80 | 2.88 | 2.40 |
| % by wt. | 84.3 | 2.5 | 3.0 | 5.7 | 2.5 | 2.0 |
| mol % | 79.0 | 5.0 | 5.0 | 10.0 | 1.00 | — |

EXAMPLE 20

| Amount | AMP5 | DMAAm | HEEA | NVP | TMPTA-EO-3 | DLP |
|---|---|---|---|---|---|---|
| g | 100.00 | 6.00 | 3.60 | 3.50 | 5.30 | 2.40 |
| % by wt. | 82.8 | 5.0 | 3.0 | 2.9 | 4.3 | 2.0 |
| mol % | 78.0 | 9.8 | 5.1 | 5.10 | 2.00 | — |

EXAMPLE 21

| Amount | AMP5 | DMAAm | MAA | GPTA | V601 |
|---|---|---|---|---|---|
| g | 100.00 | 12.60 | 0.27 | 2.29 | 1.50 |
| % by wt. | 85.7 | 10.8 | 0.2 | 2.0 | 1.3 |
| mol % | 78.0 | 20.6 | 0.55 | 0.85 | — |

EXAMPLE 22

| Amount | AMP5 | DMAAm | MAA | GPTA | V601 |
|---|---|---|---|---|---|
| g | 100.00 | 12.60 | 1.35 | 2.29 | 1.40 |
| % by wt. | 85.0 | 10.7 | 1.2 | 1.9 | 1.2 |
| mol % | 76.5 | 20.15 | 2.5 | 0.85 | — |

EXAMPLE 23

| Amount | AMP5 | DMAAm | MAA | GPTA | V601 |
|---|---|---|---|---|---|
| g | 100.00 | 13.00 | 2.80 | 2.36 | 1.50 |
| % by wt. | 83.6 | 10.9 | 2.3 | 2.0 | 1.2 |
| mol % | 74.0 | 20.15 | 5.0 | 0.85 | — |

EXAMPLE 24

| Amount | AMP5 | DMAAm | MAA | GPTA | V601 |
|---|---|---|---|---|---|
| g | 100.00 | 13.80 | 4.40 | 2.47 | 1.60 |
| % by wt. | 81.8 | 11.3 | 3.6 | 2.0 | 1.3 |
| mol % | 71.1 | 20.5 | 7.55 | 0.85 | — |

EXAMPLE 25

| Amount | AMP5 | DMAAm | MAA | GPTA | V601 |
|---|---|---|---|---|---|
| g | 100.00 | 13.95 | 6.00 | 2.54 | 1.70 |
| % by wt. | 80.5 | 11.2 | 4.8 | 2.1 | 1.4 |
| mol % | 69.1 | 20.1 | 9.95 | 0.85 | — |

EXAMPLE 26

| Amount | AMP5 | DMAAm | MAA | GPTA | V601 |
|---|---|---|---|---|---|
| g | 100.00 | 14.90 | 9.60 | 2.54 | 1.70 |
| % by wt. | 77.7 | 11.6 | 7.5 | 2.0 | 1.2 |
| mol % | 64.3 | 20.0 | 14.9 | 0.8 | — |

EXAMPLE 27

| Amount | AMP5 | DMAAm | MAA | NVP | GPTA | V601 |
|---|---|---|---|---|---|---|
| g | 100.00 | 13.20 | 2.85 | 0.75 | 2.39 | 1.20 |
| % by wt. | 83.1 | 11.0 | 2.4 | 0.5 | 2.0 | 1.0 |
| mol % | 73.0 | 20.05 | 5.0 | 1.0 | 0.84 | — |

EXAMPLE 28

| Amount | AMP5 | DMAAm | MAA | NVP | TMPTA-PO-3 | V601 |
|---|---|---|---|---|---|---|
| g | 100.00 | 13.20 | 2.85 | 0.75 | 2.60 | 1.20 |
| % by wt. | 82.9 | 10.9 | 2.4 | 0.6 | 2.2 | 1.0 |
| mol % | 73.0 | 20.05 | 5.1 | 1.0 | 0.85 | — |

EXAMPLE 29

| Amount | AMP5 | DMAAm | MAA | NVP | TMPTA-EO-3 | V601 |
|---|---|---|---|---|---|---|
| g | 100.00 | 13.20 | 2.85 | 0.75 | 2.40 | 1.20 |
| % by wt. | 83.1 | 11.0 | 2.4 | 0.5 | 2.0 | 1.0 |
| mol % | 73.0 | 20.05 | 5.1 | 1.0 | 0.85 | — |

EXAMPLE 30

| Amount | AMP5 | DMAAm | MAA | NVP | GP15TA | V601 |
|---|---|---|---|---|---|---|
| g | 100.00 | 13.20 | 2.85 | 0.75 | 3.70 | 1.20 |
| % by wt. | 82.2 | 10.8 | 2.3 | 0.6 | 3.1 | 1.0 |
| mol % | 73.0 | 20.05 | 5.1 | 1.0 | 0.85 | — |

EXAMPLE 31

| Amount | AMP5 | DMAAm | HEEA | MAA | GPTA | V601 |
|---|---|---|---|---|---|---|
| g | 100.00 | 2.85 | 3.30 | 2.49 | 2.45 | 1.40 |
| % by wt. | 88.9 | 2.5 | 2.9 | 2.2 | 2.3 | 1.2 |
| mol % | 84.0 | 5.0 | 5.0 | 5.0 | 1.00 | — |

EXAMPLE 32

| Amount | AMP5 | DMAAm | HEEA | MAA | GP15TA | V601 |
|---|---|---|---|---|---|---|
| g | 100.00 | 6.45 | 7.50 | 2.85 | 4.30 | 1.50 |
| % by wt. | 81.6 | 5.3 | 6.1 | 2.3 | 3.5 | 1.2 |
| mol % | 74.0 | 10.0 | 10.0 | 5.0 | 1.00 | — |

EXAMPLE 33

| Amount | AMP5 | DMAAm | HEEA | MAA | TMPTA-EO-3 | V601 |
|---|---|---|---|---|---|---|
| g | 100.00 | 3.42 | 16.00 | 3.00 | 3.00 | 1.60 |
| % by wt. | 78.7 | 2.7 | 12.6 | 2.4 | 2.4 | 1.2 |
| mol % | 69.1 | 4.9 | 20 | 5.0 | 1.00 | — |

EXAMPLE 34

| Amount | AMP5 | DMAAm | HEEA | MAA | TMPTA-PO-3 | V601 |
|---|---|---|---|---|---|---|
| g | 100.00 | 9.66 | 3.75 | 2.80 | 3.05 | 1.50 |
| % by wt. | 82.8 | 8.0 | 3.2 | 2.3 | 2.5 | 1.2 |
| mol % | 74.0 | 15.0 | 5.0 | 5.0 | 1.00 | — |

EXAMPLE 35

| Amount | AMP5 | DMAAm | HEEA | MAA | TMPTA-PO-3 | V601 |
|---|---|---|---|---|---|---|
| g | 100.00 | 9.66 | 3.75 | 2.80 | 6.20 | 1.50 |
| % by wt. | 80.7 | 7.8 | 3.0 | 2.3 | 5.0 | 1.2 |
| mol % | 73.3 | 14.8 | 4.9 | 4.9 | 2.00 | 1.0 |

EXAMPLE 36

| Amount | AMP5 | HEEA | GPTA | V601 |
|---|---|---|---|---|
| g | 95.00 | 13.30 | 1.23 | 1.40 |
| % by wt. | 85.6 | 12.0 | 1.1 | 1.3 |
| mol % | 79.5 | 20.0 | 0.50 | — |

EXAMPLE 37

| Amount | AMP5 | HEEA | GPTA | V601 |
|---|---|---|---|---|
| g | 95.00 | 13.30 | 1.85 | 1.40 |
| % by wt. | 85.2 | 11.9 | 1.7 | 1.3 |
| mol % | 79.3 | 20.0 | 0.75 | — |

EXAMPLE 38

| Amount | AMP5 | HEEA | GPTA | V601 |
|---|---|---|---|---|
| g | 95.00 | 13.40 | 2.49 | 1.40 |
| % by wt. | 84.6 | 12.0 | 2.2 | 1.2 |
| mol % | 78.9 | 20.1 | 1.00 | — |

EXAMPLE 39

| Amount | AMP5 | DMAAm | GPTA | V601 |
|---|---|---|---|---|
| g | 95.00 | 11.40 | 1.04 | 1.30 |
| % by wt. | 87.3 | 10.5 | 1.0 | 1.2 |
| mol % | 79.6 | 19.98 | 0.42 | — |

EXAMPLE 40

| Amount | AMP5 | DMAAm | GPTA | V601 |
|---|---|---|---|---|
| g | 95.00 | 11.40 | 1.39 | 1.30 |
| % by wt. | 87.1 | 10.5 | 1.3 | 1.2 |
| mol % | 79.5 | 19.95 | 0.56 | — |

EXAMPLE 41

| Amount | AMP5 | DMAAm | GPTA | V601 |
|---|---|---|---|---|
| g | 95.00 | 11.40 | 1.74 | 1.30 |
| % by wt. | 86.8 | 10.4 | 1.6 | 1.2 |
| mol % | 79.4 | 19.9 | 0.70 | — |

EXAMPLE 42

| Amount | AMP5 | DMAAm | GPTA | V601 |
|---|---|---|---|---|
| g | 95.00 | 11.40 | 2.81 | 1.30 |
| % by wt. | 86.0 | 10.3 | 2.5 | 1.2 |
| mol % | 79.1 | 19.8 | 1.1 | — |

EXAMPLE 43

| Amount | AMP5 | DMAAm | GPTA | V601 |
|---|---|---|---|---|
| g | 95.00 | 8.10 | 0.98 | 1.30 |
| % by wt. | 90.1 | 7.7 | 0.9 | 1.2 |
| mol % | 84.5 | 15.1 | 0.4 | — |

EXAMPLE 44

| Amount | AMP5 | DMAAm | GPTA | V601 |
|---|---|---|---|---|
| g | 95.00 | 8.15 | 1.64 | 1.30 |
| % by wt. | 89.5 | 7.8 | 1.5 | 1.2 |
| mol % | 84.2 | 15.10 | 0.70 | — |

EXAMPLE 45

| Amount | AMP5 | DMAAm | GPTA | V601 |
|---|---|---|---|---|
| g | 95.00 | 8.20 | 2.31 | 1.30 |
| % by wt. | 88.9 | 7.7 | 2.2 | 1.2 |
| mol % | 83.9 | 15.1 | 1.0 | — |

EXAMPLE 46

| Amount | AMP5 | DMAAm | GPTA | V601 |
|---|---|---|---|---|
| g | 95.00 | 5.15 | 0.93 | 1.20 |
| % by wt. | 92.9 | 5.0 | 0.9 | 1.2 |
| mol % | 89.4 | 10.2 | 0.4 | — |

EXAMPLE 47

| Amount | AMP5 | DMAAm | GPTA | V601 |
|---|---|---|---|---|
| g | 95.00 | 5.15 | 1.55 | 1.20 |
| % by wt. | 92.3 | 5.0 | 1.5 | 1.2 |
| mol % | 89.2 | 10.1 | 0.70 | — |

EXAMPLE 48

| Amount | AMP5 | DMAAm | GPTA | V601 |
|---|---|---|---|---|
| g | 95.00 | 5.15 | 2.18 | 1.20 |
| % by wt. | 91.7 | 5.0 | 2.1 | 1.2 |
| mol % | 88.9 | 10.1 | 1.0 | — |

EXAMPLE 49

| Amount | AMP5 | DMAAm | GPTA | V601 |
|---|---|---|---|---|
| g | 100.00 | 2.55 | 1.55 | 1.20 |
| % by wt. | 95.0 | 2.4 | 1.5 | 1.1 |
| mol % | 94.3 | 5.0 | 0.7 | — |

EXAMPLE 50

| Amount | AMP5 | DMAAm | GPTA | V601 |
|---|---|---|---|---|
| g | 100.00 | 2.55 | 2.18 | 1.20 |
| % by wt. | 94.4 | 2.4 | 2.1 | 1.1 |
| mol % | 94.0 | 5.01 | 0.99 | — |

B) Examples Relating to Thickening in the Presence of Salt and Relating to Sensory Properties of Polymers According to the Invention B1) Thickening in the Presence of Salt Polymers according to the invention bring about a higher viscosity in the presence of salt than the polymer Aristoflex® AVC from Clariant from the prior art. The viscosities were ascertained at a polymer concentration of 2% by weight in a solution of 2% by weight of sodium chloride in water.

The viscosities were measured using a Brookfield viscosimeter model DV II, the spindles from the spindle set RV at 20 revolutions/minute and 20° C. Spindles 1 to 7 from the spindle set RV are used. Under these measuring conditions, spindle 1 is chosen for viscosities of at most 500 mPa·s, spindle 2 for viscosities of at most 1000 mPa·s, spindle 3 for viscosities of at most 5000 mPa·s, spindle 4 for viscosities of at most 10 000 mPa·s, spindle 5 for viscosities of at most 20 000 mPa·s, spindle 6 for viscosities of at most 50 000 mPa·s and spindle 7 for viscosities of at most 200 000 mPa·s.

| Polymer | Viscosity (2% by weight of polymer in a solution of 2% by weight of NaCl in water) [mPa · s] |
|---|---|
| Aristoflex ® AVC (comparison) | 3680 |
| Example 36 | 6740 |
| Example 37 | 7940 |
| Example 38 | 5800 |
| Example 39 | 5230 |
| Example 40 | 4600 |
| Example 41 | 5540 |
| Example 2 | 4760 |
| Example 42 | 4160 |
| Example 43 | 3890 |
| Example 44 | 7160 |
| Example 45 | 6320 |
| Example 46 | 3810 |
| Example 47 | 6140 |
| Example 48 | 7360 |
| Example 49 | 6000 |
| Example 50 | 5500 |
| Example 15 | 5480 |
| Example 23 | 5600 |
| Example 27 | 6700 |

B2) Sensory Properties

Additionally, sensory tests were carried out within a panel test with 10 subjects, the sensory properties of the polymers according to the invention being tested using the following base formulation:

| Ingredient | % by wt. |
|---|---|
| Myritol 318 | 3 |
| Cetiol MM | 2.5 |
| Lanette O | 2 |
| Imwitor 370P | 1 |
| Eutanol G | 1 |
| Polymer | 0.4 |
| Water | ad 100 |
| Glycerol | 7.5 |
| Ethanol | 3 |
| Tocopheryl acetate | 1 |
| Aloe Barbadensis | 1 |
| NaOH (10% by wt. in water) | 0.2 |
| Phenonip | 0.6 |

Here, formulations were prepared using the polymers specified below, with Aristoflex® AVC (a polymer according to EP 1 116 733 based on 2-acrylamido-2-methylpropanesulfonic acid, vinylpyrrolidone and trimethylolpropane triacrylate as crosslinker) being used as comparison polymer, and assessed sensorily. The overall assessment of the polymers was evaluated using the key ++=very good, +=good, o=satisfactory, −=unsatisfactory.

| Polymer | Sensory properties | Overall assessment |
|---|---|---|
| Aristoflex ® AVC (comparison) | absorbs rapidly, short-term caring | — |
| Example 39 | absorbs slowly, film lies on the skin, caring | o |
| Example 40 | absorbs slowly, film lies on the skin, caring | o |
| Example 41 | absorbs slowly, long-term caring | + |

| Polymer | Sensory properties | Overall assessment |
|---|---|---|
| Example 2 | absorbs slowly, very long-term caring | ++ |
| Example 42 | absorbs slowly, very long-term caring | ++ |
| Example 36 | absorbs slowly, long-term caring | + |
| Example 37 | absorbs slowly, very long-term caring | ++ |
| Example 38 | absorbs slowly, very long-term caring | ++ |
| Example 43 | absorbs slowly, long-term caring | + |
| Example 44 | absorbs slowly, very long-term caring | ++ |
| Example 45 | absorbs slowly, very long-term caring | ++ |
| Example 46 | absorbs very slowly, caring | o |
| Example 47 | absorbs very slowly, caring | o |
| Example 48 | absorbs very slowly, caring | o |
| Example 49 | absorbs slowly, caring | o |
| Example 50 | absorbs slowly, caring | o |
| Example 15 | absorbs slowly, very long-term caring | ++ |
| Example 23 | absorbs relatively slowly, film lies on the skin, relatively rich, long-term caring | ++ |
| Example 27 | absorbs slowly, caring | o |

C) Examples Relating to Cosmetic Formulations According to the Invention

In the examples, all of the following percentages are percentages by weight (% by wt.), unless explicitly stated otherwise.

The following cosmetic formulations were prepared with polymers according to the invention:

FORMULATION EXAMPLES 1-8

Hand Sanitizer Formulations

| Formulation No. | 1 | 2 | 3 | 4 | 5 | 6 | 7 | 8 |
|---|---|---|---|---|---|---|---|---|
| Ingredient | Amount of the respective ingredient [% by wt.] | | | | | | | |
| Polymer as in Ex. 2 | 1.0 | — | 1.2 | — | 0.8 | — | 1.0 | — |
| Polymer as in Ex. 27 | — | 1.0 | — | 1.2 | — | 1.0 | — | 1.0 |
| Ethanol (96% by wt. in water) | 70.0 | 40.0 | — | — | — | 40.0 | 70.0 | 50.0 |
| Isopropanol | — | — | 40.0 | 70.0 | 70.0 | — | — | — |
| Piroctone olamine | — | — | — | — | 1.0 | 0.5 | — | 1.0 |
| Triclosan | — | — | — | — | — | — | 0.5 | — |
| Water | 29.0 | 59.0 | 58.8 | 28.8 | 28.2 | 58.5 | 28.5 | 48.0 |

Preparation:

The polymer is stirred into water, the corresponding alcohol, in which antibacterial active ingredients such as piroctone olamine or triclosan may be dissolved, is added and homogenized. This results in a clear gel.

FORMULATION EXAMPLES 9-12

Hair Care Gels for Strong Hold and Excellent Styling

| | Formulation No. | | | |
|---|---|---|---|---|
| | 9 | 10 | 11 | 12 |
| Ingredient | Amount of the respective ingredient [% by wt.] | | | |
| Polymer as in example 6 | 1.0 | — | 1.0 | — |
| Polymer as in example 23 | — | 1.0 | — | 1.0 |
| Sorbitol | 0.5 | 0.5 | — | — |
| Water | ad 100 | ad 100 | ad 100 | ad 100 |
| Carbomer | — | 0.5 | 0.5 | — |
| NaOH | — | q.s. | q.s. | — |
| PEG-40 hydrogenated castor oil | 1.0 | 1.0 | 1.0 | — |
| Fragrance | 0.3 | 0.3 | — | 0.3 |
| Ethanol (96% by wt. in water) | 10.0 | 10.0 | 5.0 | — |
| Diaformer Z-712 N (acrylates/lauryl acrylates/stearyl acrylate/ethylamine oxide methacrylate) | 4.5 | 4.5 | — | 6.0 |
| Luviskol VA 64 (PVP/VA) | 3.0 | 3.0 | 5.0 | — |
| Propylene glycol | 1.0 | 1.0 | — | 1.0 |
| Panthenol | 0.5 | 0.5 | — | — |
| Dyestuff solution | q.s. | q.s. | q.s. | — |
| Phenoxyethanol | 1.0 | 1.0 | 0.5 | 0.7 |

Preparation:

The polymers as in examples 1 and 2 are dissolved in water (and optionally sorbital). If carbomer is added, then NaOH is used to neutralize the mixture to pH=7. The other components are optionally mixed with PEG-40 hydrogenated castor oil and stirred into the thickened water phase.

FORMULATION EXAMPLE 13

Oxidative Hair Coloring Formulation

Color Base:

| Ingredient | % by wt. |
|---|---|
| Polyquaternium-29 (Dihydroxyproyl chitosan trimonium chloride) | 0.5 |
| m-Phenylenediamine | 0.08 |
| p-Phenylenediamine HCl | 0.30 |
| Resorcinol | 0.25 |
| Sodium bisulfate | 0.30 |
| Sodium laureth sulfate | 3.50 |
| Cetyl Alcohol | 15.00 |
| Ammonia (25% strength by weight, aqueous) | 2.00 |
| Water | ad 100 |

Preparation:

Cetyl alcohol and sodium laureth sulfate are heated to 60° C., mixed and introduced, with stirring, into the water phase, in which the other ingredients have been dissolved.

Developer Gel:

| Ingredient | % by wt. |
|---|---|
| Polymer as in example 6 | 1.5 |
| Hydrogen peroxide (35% strength by weight, aqueous) | 18 |
| Sodium pyrophosphate | 0.02 |
| 4-Methyl-6-(cyclohexyl)-1-hydroxy-2-pyridone | 0.002 |
| Propylene glycol | 1 |
| Water | ad 100 |

Preparation:

4-Methyl-6-(cyclohexyl)-1-hydroxy-2-pyridone is dissolved in propylene glycol. The polymer according to the invention is dissolved in water, then the hydrogen peroxide solution is stirred in, followed by the stabilizer sodium pyrophosphate and also the propylene glycol solution.

This produces a gel with a viscosity of ca. 3000 mPa·s at 20° C.

Coloring Procedure:

50 ml of the color base are stirred with 50 ml of the developer gel and applied to the hair. After 30 minutes, it is rinsed out.

FORMULATION EXAMPLE 14

Emulsifier-Free Hair Bleaching Gel

| Ingredient | % by wt. |
| --- | --- |
| Polymer as in example 27 | 1.0 |
| Hydrogen peroxide (35% strength by weight, aqueous) | 17 |
| Sodium pyrophosphate | 0.02 |
| Sodium stannate | 0.04 |
| 4-Methyl-6-(2,4,4-trimethylpentyl)-1-hydroxy-2-pyridone | 0.001 |
| Propylene glycol | 1 |
| Water | ad 100 |

Preparation:

4-Methyl-6-(2,4,4-trimethylpentyl)-1-hydroxy-2-pyridone is dissolved in propylene glycol. The polymer is dissolved in water, then the hydrogen peroxide solution is stirred in, followed by the two stabilizers and the propylene glycol solution.

FORMULATION EXAMPLE 15

Fixing Gel for Permanent Waves

| Ingredient | % by wt. |
| --- | --- |
| Polymer as in example 23 | 0.8 |
| Hydrogen peroxide (35% strength by weight, aqueous) | 5 |
| Sodium pyrophosphate | 0.02 |
| 4-Methyl-6-(2,4,4-trimethylpentyl)-1-hydroxy-2-pyridone | 0.002 |
| Propylene glycol | 1 |
| Water | ad 100 |

Preparation:

4-Methyl-6-(2,4,4-trimethylpentyl)-1-hydroxy-2-pyridone is dissolved in propylene glycol.

The polymer is dissolved in water, the hydrogen peroxide solution and the pyrophosphate and also the propylene glycol solution are introduced and homogenized.

Formulation Example 16

O/W Exfoliating Cream with a High Electrolyte Content (Na-glycolate)

| Phase | Ingredient | % by wt. |
| --- | --- | --- |
| A | PEG-120 Methyl glucose dioleate | 1.5 |
| B | Water | ad 100 |

-continued

| Phase | Ingredient | % by wt. |
| --- | --- | --- |
| C | Mineral oil | 5.0 |
|   | Caprylyl trimethicone | 3.0 |
| D | Polymer as in example 2 | 1.2 |
| E | Glycolic acid 30% by weight in water (neutralized with NaOH to pH = 4) | 6.0 |
|   | Preservative | q.s. |
| F | Laureth-7 | 3.0 |

Preparation:

Dissolve A in phase B with heating. Disperse phase C into phase D and stir into the water phase. Then stir in phases E and F.

FORMULATION EXAMPLE 17

W/O Care Skin Milk

| Phase | Ingredient | % by wt. |
| --- | --- | --- |
| A | Amodimethicone glycerocarbamate | 2.0 |
|   | Cyclopentasiloxane | 5.0 |
|   | Paraffin oil | 3.5 |
|   | Apricot kernel oil | 1.0 |
|   | Grape seed oil | 0.5 |
|   | Microcrystalline wax | 0.7 |
|   | Stearic acid | 0.5 |
|   | Ethylhexyl cocoate | 7.0 |
| B | Polymer as in example 27 | 0.3 |
| C | Water | ad 100 |
|   | Glycerol | 3.5 |
|   | Preservative | q.s. |

Preparation:

Heat the oil phase A to 80° C. and stir in the polymer B. Slowly add phase C in small portions with vigorous stirring and leave to cool to room temperature.

FORMULATION EXAMPLE 18

Make-Up Remover with Excellent Skin Feel

| Phase | Ingredient | % by wt. |
| --- | --- | --- |
| A | Isopropyl C12-15 pareth-9 carboxylate | 5.0 |
| B | Sodium cocoyl glutamate (25% by strength by weight solution in water) | 2.3 |
|   | Cocamidopropyl betaine (30% strength by weight solution in water) | 3.0 |
|   | Laureth-7 | 2.0 |
|   | Water | ad 100 |
|   | Allantoin | 0.3 |
|   | Polypropylene terephthalate | 1.0 |
|   | 1,6 Hexanediol | 2.0 |
|   | Propylene glycol | 2.0 |
|   | PEG-8 | 2.0 |
|   | Panthenol | 0.5 |
|   | Poloxamer 407 | 3.0 |
|   | Preservative | q.s. |
|   | Polymer as in example 6 | 1.0 |

Preparation:

Dissolve the components of B in A one after the other

FORMULATION EXAMPLE 19

Shampoo/Shower Bath with Suspended Particles

| Phase | Ingredient | % by wt. |
|---|---|---|
| A | Water | ad 100 |
| B | Polymer as in example 2 | 2.0 |
| C | Sodium laureth sulfate (30% by weight in water) | 18.5 |
|   | Perfume | 0.5 |
|   | Preservative | q.s. |
| D | Sodium cocoyl glutamate (25% strength by weight solution in water) | 20.0 |
| E | Synthetic wax | 0.2 |

Preparation:

Dissolve polymer in water, then introduce phases C, D and E one after the other and homogenize.

FORMULATION EXAMPLE 20

Clear Deodorizing Gel

| Phase | Ingredient | % by wt. |
|---|---|---|
| A | PEG-40 hydrogenated castor oil | 1.0 |
|   | Perfume | 0.1 |
| B | Ethanol (96% by weight in water) | 25.0 |
|   | Piroctone olamine (Octopirox ®, Clariant) | 0.1 |
| C | Propylene glycol | 20.0 |
|   | Diisopropyl adipate | 1.0 |
|   | Water | ad 100 |
|   | Benzyl alcohol, methylparaben, propylparaben | 0.2 |
| D | Polymer as in example 23 | 1.3 |
| E | Citric acid | q.s. |

Preparation:

Phase A is mixed, then phase B and phase C are added one after the other and the pH is adjusted to pH=5.5 using phase E. Finally, phase D is stirred in until a homogeneous clear gel is formed.

FORMULATION EXAMPLE 21

Mattifying Serum

| Phase | Ingredient | % by wt. |
|---|---|---|
| A | Water | ad 100 |
| B | Glycerol | 3.0 |
|   | Polymer as in example 23 | 0.5 |
|   | Caprylyl methicone | 1.5 |
|   | Cyclomethicone and dimethicone crosspolymer (Dow Corning 9040 Silicone Elastomer blend) | 1.0 |
|   | Fragrance | 0.15 |
|   | Preservative | q.s. |

Preparation:

The components of B are stirred into phase A one after the other.

FORMULATION EXAMPLE 22

Skin Whitening Gel

| Phase | Ingredient | % by wt. |
|---|---|---|
| A | Allantoin | 0.5 |
| B | Water | ad 100 |
| C | Xanthan gum | 0.5 |
| D | Ascorbic acid 2-glucoside | 2.0 |
| E | NaOH (25% strength by weight solution in water) | q.s. |
| F | Glycerol | 10.0 |
|   | Ethanol (96% by weight in water) | 10.0 |
|   | PEG/PPG-18/18 Dimethicone (Dow Corning ® 190, Dow Corning) | 1.0 |
|   | PEG-40 hydrogenated castor oil | 0.8 |
| G | Polymer as in example 27 | 1.0 |
| H | NaOH (25% strength by weight solution in water) | q.s. |
| I | DMDM Hydantoin | q.s |

Preparation:

Phase A is dissolved in phase B with heating, phase C is stirred in, phase D is added and the pH is adjusted to 6.5 using phase E. Phase F is mixed and then added, then phase G is added and stirred until a homogeneous gel is achieved. Phase H is used to adjust the pH where necessary to 6.5 and the preservative I is stirred in.

FORMULATION EXAMPLE 23

Elegant O/W Skincare Body Lotion with Low Stickiness

| Phase | Ingredient | % by wt. |
|---|---|---|
| A | Caprylic/capric triglyceride | 3.5 |
|   | myristyl myristate | 2.5 |
|   | Cetearyl alcohol | 2.0 |
|   | Glyceryl stearate citrate | 1.0 |
|   | Octyldodecanol | 1.0 |
| B | Polymer as in example 17 | 0.6 |
| C | Water | ad 100 |
|   | Glycerol | 7.5 |
| D | Ethanol (96% by weight in water) | 3.0 |
|   | Dimethicone | 3.0 |
|   | Tocopheryl acetate | 1.0 |
|   | *Aloe Barbadensis* | 1.0 |
|   | Preservative | q.s. |
|   | Fragrance | q.s. |
| E | NaOH (10% by weight in water) | q.s. |

Preparation:

Phase A is melted at 70° C., phase B is sprinkled in and phase C is heated to 70° C. and stirred in. After cooling to 35° C., phase D is stirred in and, finally, the pH is adjusted to 6 using phase E.

FORMULATION EXAMPLE 24

Surfactant-Free Anti-Aging O/W Gel Cream with Skin Wrinkle-Reducing Function

| Phase | Ingredient | % by wt. |
|---|---|---|
| A | Dicaprylyl ether | 5.0 |
|   | Caprylic/capric triglyceride | 5.0 |

-continued

| Phase | Ingredient | % by wt. |
|---|---|---|
|  | Cetearyl alcohol | 2.0 |
|  | Preservative | q.s. |
| B | Ubiquinone | 0.1 |
| C | Polymer as in example 23 | 1.1 |
| D | Sodium hyaluronate (Dekluron) | 0.3 |
|  | glycerol | 8.0 |
| E | Water | ad 100 |
|  | Mica and titanium dioxide and tin oxide (Prestige ® Soft Orange, Eckart) | 0.5 |
| F | Tocopheryl acetate | 0.3 |
| G | NaOH (10% by weight in water) | q.s |

Preparation:
Phase A is melted at 80° C., and phase B and phase C are stirred in one after the other. Phase D is predissolved in phase E and added. Phase F is stirred in at 35° C. and phase G is used to adjust the pH to 6.0. This gives a gel cream.

FORMULATION EXAMPLE 25

Surfactant-Free Anti-Aging O/W Gel Cream

| Phase | Ingredient | % by wt. |
|---|---|---|
| A | Dicaprylyl ether | 5.0 |
|  | Caprylic/capric triglyceride | 5.0 |
|  | Cetearyl alcohol | 2.0 |
|  | Preservative | q.s. |
| B | Ubiquinone | 0.1 |
| C | Polymer as in example 27 | 1.1 |
| D | Xanthan gum | 0.2 |
|  | Glycerol | 8.0 |
| E | Water | ad 100 |
|  | Mica and titanium dioxide and tin oxide (Prestige ® Soft Orange, Eckart) | 0.5 |
| F | Tocopheryl acetate | 0.3 |
| G | NaOH (10% by weight in water) | q.s |

Preparation:
Phase A is melted at 80° C., and phase B and phase C are stirred in one after the other. Phase D is predissolved in phase E and added. Phase F is stirred in at 35° C. and phase G is used to adjust the pH to 6.0. This gives a gel cream.

FORMULATION EXAMPLE 26

O/W Self-Tanning Cream with Moisturizing Effect

| Phase | Ingredient | % by wt. |
|---|---|---|
| A | Cetyl phosphate | 1.0 |
|  | Glyceryl stearate | 0.5 |
|  | Cetearyl alcohol | 0.5 |
|  | Isohexadecane | 8.0 |
|  | Isopropyl palmitate | 7.0 |
|  | Caprylyl Methicone | 1.0 |
| B | Polymer as in example 6 | 1.0 |
| C | Water | ad 100 |
|  | Sodium cocoyl glutamate | 0.5 |
|  | Glycerol | 5.0 |
|  | NaOH (10% by weight in water) | 0.5 |
| D | Tocopheryl acetate | 1.0 |
|  | Fragrance | 0.2 |
|  | Preservative | q.s. |
| E | Dihydroxyacetone | 5.0 |
|  | Water | 8.0 |

Preparation:
Phase A is melted at 80° C., phase B and phase C are stirred in one after the other. Phase D is added at 30° C. and finally phase E is stirred in. This results in a cream with a pH of 4.2.

FORMULATION EXAMPLES 27-32

W/O Sunscreen Formulations with a High Protection Factor

In sunscreen compositions, the polymers according to the invention contribute to better distributability of the sunscreen formulation and give the cosmetic and pharmaceutical product a pleasant skin feel and good spreading ability.

The sunscreen formulations shown in the table below were prepared.

| Formulation No. Ingredient | 27 | 28 | 29 | 30 | 31 | 32 |
|---|---|---|---|---|---|---|
| $C_{12-15}$ Alkyl benzoate | 8 | 8 | 8 | 8 | 8 | 8 |
| Caprylic capric triglyceride | 5 | 5 | 5 | 5 | 5 | 5 |
| Octocrylene | 9 | — | 5 | 4 | — | — |
| Ethylhexyl methoxy-cinnamate | 7 | 7 | 7 | — | 6 | 6 |
| Butyl methoxy-dibenzoyl-methane | 2.5 | — | 2.5 | — | — | — |
| Disodium phenyl dibenzimidazole tetrasulfonate | — | — | — | — | — | 3 |
| Ethylhexyl bis-isopentyl-bezoxazolyl-phenyl-melamine | — | — | — | — | 2 | — |
| Diethylamino hydroxybenzoyl hexyl benzoate | — | — | 2 | 1 | — | — |
| Bis-ethylhexyloxy-phenol methoxyphenyl triazine | — | 3 | — | 2 | 4 | 3 |
| Methylene bis-benzotriazolyl tetramethylbutyl-phenol | — | 3 | — | — | — | 2 |
| Ethylhexyl triazone | — | — | — | 3 | — | — |
| Diethylhexyl butamido triazone | — | — | — | — | 2 | — |
| Polysilicone-15 | — | — | 2 | — | — | — |
| Phenyl-benzimidazole sulfonic acid | — | — | — | 3 | — | — |
| Titanium dioxide | — | 5 | 3 | 4 | 5 | 5 |
| Cetearyl alcohol | 1 | 1 | 1 | 1 | 1 | 1 |
| Sunflower seed oil sorbitol esters | 2 | 2 | 2 | 2 | 2 | 2 |
| Preservative | q.s. | q.s. | q.s. | q.s. | q.s. | q.s. |
| Potassium cetyl phosphate | 3 | 3 | 3 | 3 | 3 | 3 |
| Polymer as in example 4 | 1 | 0.6 | — | — | — | — |
| Polymer as in example 23 | — | — | 0.5 | 0.9 | — | — |
| Polymer as in example 27 | — | — | — | — | 1 | 1 |
| Water | ad 100 | ad 100 | ad 100 | ad 100 | ad 100 | ad 100 |

-continued

| Formulation No. | 27 | 28 | 29 | 30 | 31 | 32 |
|---|---|---|---|---|---|---|
| Ingredient | Amount of the respective ingredient [% by wt.] | | | | | |
| Nylon | — | 0.5 | — | — | — | — |
| Bis-ethylhexyl hydroxy-dimethoxy benzylmalonate | — | — | 1 | — | — | — |
| Talc | — | — | — | — | 0.5 | — |

Preparation:

For the preparation, the oil-soluble components were heated to 80° C., potassium cetyl phosphate and the polymer according to the invention were sprinkled in one after the other and the combined water-soluble phases were slowly introduced into the oil phase with vigorous stirring. The emulsions formed were left to cool to room temperature with stirring.

The sun protection filters used in the formulation examples 27-32, their trade names and their UV protection range are listed in the table below.

| Sunscreen filter | Trade name | Protection range (UV-A/UV-B) |
|---|---|---|
| Octocylene | Neo Heliopan ® 303 | B |
| Ethylhexyl methoxycinnamate | Neo Heliopan ® AV | B |
| Butyl methoxydibenzoylmethane | Neo Heliopan ® 357, Parsol ® 1789 | A |
| Disodium phenyl dibenzimidazole tetrasulfonate | Neo Heliopan ® AP | A |
| Ethylhexyl bis-isopentylbezoxazolylphenyl-melamine | Uvasorb ® K2A | A |
| Diethylamino hydroxybenzoyl hexyl benzoate | Uvinul ® A Plus | A |
| Bis ethylhexyloxyphenol Methoxyphenyl triazine | Tinosorb ® S | A/B |
| Methylene bis-benzotriazolyl tetramethylbutylphenol | Tinosorb ® M | A/B |
| Ethylhexyl triazone | Uvinul ® T 150 | B |
| Diethylhexyl butamido triazone | Uvasorb ® HEB | B |
| Polysilicone-15 | Parsol ® SLX | B |
| Phenylbenzimidazole sulfonic acid | | B |

FORMULATION EXAMPLE 33

O/W Sunscreen Cream

| Phase | Ingredient | % by wt. |
|---|---|---|
| A | Ethylhexyl methoxycinnamate | 6.0 |
| | Ethylhexyltriazone | 2.0 |
| | Benzophenone-3 | 2.0 |
| | BHT | 0.05 |
| B | Polymer as in example 2 | 1.5 |
| | Trilaureth-4 phosphate | 2.0 |
| | Polyglyceryl-2 sesquiisostearate | 1.0 |
| | Caprylyl methicone | 1.0 |
| | Phenonip ®, Clariant | 0.6 |
| | PVP/Hexadecene copolymer | 1.0 |
| | Tocopheryl acetate | 0.5 |
| | Fragrance | 0.2 |
| C | Water | ad 100 |
| | Disodium EDTA | 0.1 |
| D | Methylene bis-benzotriazolyl tetramethylbutylphenol | 4.0 |
| E | With triethanolamine to pH 6.8-7.2 | q.s. |

Preparation:

Homogenize phase A and dissolve at 60° C. and stir into phase B, then add phase C with stirring and stir at 300 revolutions per minute. Then, phase D is stirred in and E is used to adjust the pH.

FORMULATION EXAMPLE 34

Sprayable O/W Lotion

| Phase | Ingredient | % by wt. |
|---|---|---|
| A | Trilaureth-4 phosphate | 1.0 |
| | Mineral oil | 8.0 |
| | Isopropyl palmitate | 3.0 |
| | Cetearyl alcohol | 0.5 |
| | Caprylic/capric triglyceride | 2.0 |
| | Glyceryl stearate | 0.5 |
| | Caprylyl methicone | 1.0 |
| B | Polymer as in example 23 | 0.4 |
| C | Water | ad 100 |
| | Glycerol | 5.0 |
| D | Fragrance | 0.3 |
| | Ethanol (96% by weight in water) | 5.0 |
| E | Preservative | q.s. |

Preparation:

Heat phase A to 60° C., stir in phase B, then add phase C with stirring and stir at 300 revolutions per minute and leave to cool. Stir in phase D at 35° C., add phase E and finally homogenize.

FORMULATION EXAMPLE 35

O/W Foundation

| Phase | Ingredient | % by wt. |
|---|---|---|
| A | Hydrogenated polydecene | 9.0 |
| | Caprylic/capric triglyceride | 5.0 |
| | Caprylyl trimethicone | 4.0 |
| | Caprylyl methicone | 3.0 |
| | Steareth-2 | 1.6 |
| | Steareth-20 | 2.4 |
| | Polymer as in example 27 | 0.4 |
| B | Kaolin | 1.5 |
| | Talc | 3.0 |
| | Iron oxide | 7.9 |
| C | Glycerol | 5.0 |
| | Water | ad 100 |
| D | Preservative | q.s. |
| | Fragrance | q.s. |

Preparation:

Heat phase A to 70° C., heat phase C to 70° C. Stir phase B into phase A, then add phase C and homogenize well. After cooling to below 40° C., add phase D and homogenize for one minute.

The invention claimed is:

1. A water-soluble or water-swellable polymer comprising:

a) 20.0 to 98.97 mol % of at least one structural unit, recurring independently of one another, of the formula (1)

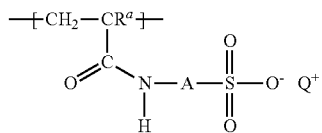

(1)

in which
R$^a$ is hydrogen, methyl or ethyl,
A is linear or branched C$_1$-C$_{12}$-alkylene, and
Q$^+$ is a counterion
and
b) 1.0 to 60.0 mol % of at least one structural unit, recurring independently of one another, of the formula (2)

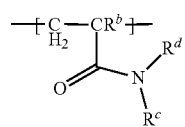

(2)

in which
R$^b$ is hydrogen, methyl or ethyl,
R$^c$ is hydrogen, a linear or branched alkyl group having 1 to 50 carbon atoms, a linear or branched mono-hydroxyalkyl group having 2 to 6 carbon atoms or a linear or branched di-hydroxyalkyl group having 2 to 6 carbon atoms,
R$^d$ is a linear or branched alkyl group having 1 to 50 carbon atoms, a linear or branched mono-hydroxyalkyl group having 2 to 6 carbon atoms or a linear or branched di-hydroxyalkyl group having 2 to 6 carbon atoms,
and
d) 0.01 to 8.0 mol % of at least one crosslinking structural unit, recurring independently of one another, of the formula (5)

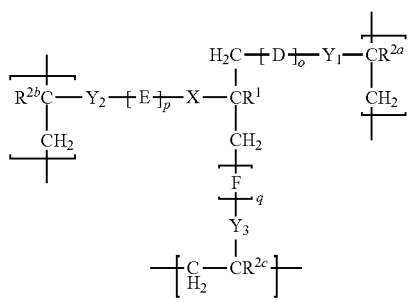

(5)

in which
R$^1$ is hydrogen, methyl, ethyl, methylol or ethylol,
R$^{2a}$, R$^{2b}$ and R$^{2c}$, in each case independently of one another, are hydrogen, methyl or ethyl,
X is a chemical bond, methylene, ethylene or a linear or branched alkylene group having 3 carbon atoms,
Y$_1$, Y$_2$ and Y$_3$, in each case independently of one another, are a chemical bond, O, CH$_2$, C(O)O, OC(O), C(O)NR$^3$ or NR$^3$C(O), R$^3$ is hydrogen or a linear or branched alkyl radical having 1 to 50 carbon atoms,
D, E and F, in each case independently of one another, are methyleneoxy, ethyleneoxy, propyleneoxy, a linear or branched alkylene group having 1 to 6 carbon atoms, a linear or branched, mono- or polyunsaturated alkenylene group having 2 to 6 carbon atoms, a linear or branched mono-hydroxyalkylene group having 2 to 6 carbon atoms or a linear or branched di-hydroxyalkylene group having 3 to 6 carbon atoms,
o, p and q, in each case independently of one another, are integers from 0 to 50, and the sum o+p+q is ≥3,
wherein it is free from structural units of the formula (10)

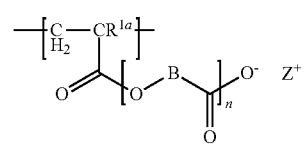

(10)

in which
R$^{1a}$ is hydrogen, methyl or ethyl,
Z$^+$ is H$^+$, NH$_4^+$, organic ammonium ions [HNR$^{5b}$R$^{6b}$R$^{7b}$]$^+$, where R$^{5b}$, R$^{6b}$ and R$^{7b}$, independently of one another, can be hydrogen, a linear or branched alkyl group having 1 to 22 carbon atoms, a linear or branched, mono- or polyunsaturated alkenyl group having 2 to 22 carbon atoms, a C$_6$-C$_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals R$^{5b}$, R$^{6b}$ and R$^{7b}$ is not hydrogen, Li$^+$, Na$^+$, K$^+$, ½ Ca$^{++}$, ½ Mg$^{++}$, ½ Zn$^{++}$ or ⅓ Al$^{+++}$ or mixtures of these ions,
B is a linear or branched alkylene group having 1 to 6 carbon atoms, and
n is an integer from 1 to 10.

2. The polymer as claimed in claim 1, wherein the at least one structural unit of the formula (1) are derived from 2-acrylamido-2-methylpropanesulfonic acid or its salts.

3. The polymer as claimed in claim 1, wherein Q$^+$ is H$^+$, NH$_4^+$, organic ammonium ions [HNR$^5$R$^6$R$^7$]$^+$, alkali metal$^+$, ½ alkaline earth metal$^{++}$, ½ Zn$^{++}$, ⅓ Al$^{+++}$ or mixtures thereof, wherein R$^5$, R$^6$ and R$^7$, independently of one another, can be hydrogen, a linear or branched alkyl group having 1 to 22 carbon atoms, a linear or branched, mono- or polyunsaturated alkenyl group having 2 to 22 carbon atoms, a C$_6$-C$_{22}$-alkylamidopropyl group, a linear mono-hydroxyalkyl group having 2 to 10 carbon atoms or a linear or branched di-hydroxyalkyl group having 3 to 10 carbon atoms, and where at least one of the radicals R$^5$, R$^6$ and R$^7$ is not hydrogen.

4. The polymer as claimed in claim 1, wherein Q$^+$ is H$^+$, NH$_4^+$ alkali metal$^+$, alkaline earth metal or mixtures thereof.

5. The polymer as claimed in claim 1, wherein the degree of neutralization of the at least one structural unit of the formula (1) is from 50.0 to 100 mol %.

6. The polymer as claimed in claim 1, wherein, in the at least one structural unit of the formula (2), R$^b$ is hydrogen or methyl, R$^c$ is H, a linear or branched alkyl group having 1 to 6 carbon atoms or a linear or branched mono-hydroxyalkyl group having 2 to 6 carbon atoms and R$^d$ is a linear or branched alkyl group having 1 to 6 carbon atoms or a linear or branched mono-hydroxyalkyl group having 2 to 6 carbon atoms.

7. The polymer as claimed in claim 1, wherein, in the at least one structural unit of the formula (5), Fe is hydrogen or ethyl, $R^{2a}$, $R^{2b}$ and $R^{2c}$, in each case independently or one another are hydrogen or methyl, X is a chemical bond or methylene, $Y_1$, $Y_2$ and $Y_3$, in each case independently of one another, are C(O)O or OC(O), D, E and F, in each case independently of one another, are ethyleneoxy or propyleneoxy, o, p and q, in each case independently of one another, are integers from 0 to 30 and the sum o+p+q is from 3 to 20.

8. The polymer as claimed in claim 7, wherein the at least one structural unit of the formula (5) are derived from at least one crosslinker selected from the group consisting of glycerol propoxylate triacrylate, trimethylolpropane propoxy triacrylate and trimethylolpropane ethoxy triacrylate.

9. The polymer as claimed in claim 1, further comprising 0.01 to 30.0 mol %, of at least one structural unit, of the formula (3)

$$\left[\begin{array}{c}C\\H_2\end{array}-CR^x\right] \quad (3)$$
(with N-C=O ring, (CH$_2$)$_m$)

in which
$R^x$ is hydrogen, methyl or ethyl and
m is an integer from 2 to 9.

10. The polymer as claimed in claim 1, further comprising 0.01 to 30.0 mol %, of at least one structural unit, of the formula (4)

$$\left[\begin{array}{c}R^y\\-C-\\C\\H_2\end{array}\right] \quad (4)$$
O=C-O$^-$ X$^+$ in which
$R^y$ is hydrogen, methyl or ethyl and
$X^+$ is a counterion.

11. The polymer as claimed in claim 1, wherein it is free from structural units of the formula (10)

$$\left[\begin{array}{c}C\\H_2\end{array}-CR^{1a}\right] \quad (10)$$
O, B, O$^-$ Z$^+$, n, O in which
$R^{1a}$ is hydrogen, methyl or ethyl,
$Z^+$ is a counterion,
B is a linear or branched alkylene group having 1 to 6 carbon atoms, and
n is an integer from 1 to 10.

12. A cosmetic, dermatological or pharmaceutical composition comprising at least one polymer as claimed in claim 1, in an amount of from 0.01 to 10.0% by weight, based on the total weight of the composition.

13. The cosmetic, dermatological or pharmaceutical composition as claimed in claim 12, wherein it is formulated on an aqueous or aqueous-alcoholic basis or is present in the form of an emulsion.

14. The cosmetic, dermatological or pharmaceutical composition as claimed in claim 12, wherein it further comprises at least one-substance selected from the group consisting of inorganic and organic salts.

15. The cosmetic, dermatological or pharmaceutical composition as claimed in claim 12, wherein it further comprises at least one substance selected from the group consisting of alpha- and beta-hydroxy acids.

16. The cosmetic, dermatological or pharmaceutical composition as claimed in claim 12, wherein it further comprises at least one substance selected from the group consisting of vitamin C and vitamin C derivatives.

17. The cosmetic, dermatological or pharmaceutical composition as claimed in claim 12, wherein it further comprises at least one substance selected from the group consisting of benzoic acid, sorbic acid, salicylic acid, lactic acid and paramethoxybenzoic acid.

18. The cosmetic, dermatological or pharmaceutical composition as claimed in claim 12, herein it further comprises at least one antimicrobial active ingredient and is present in the form of a disinfection gel.

19. The cosmetic, dermatological or pharmaceutical composition as claimed in claim 12, wherein it further comprises at least one substance selected from the group consisting of inorganic and organic UV filters and is present in the form of a sunscreen composition.

20. The cosmetic, dermatological or pharmaceutical composition as claimed in claim 12, wherein it has a pH of from 2 to 10.

21. A thickener, consistency regulator, emulsifier, sensory additive, solubilizer, dispersant, lubricant, adhesive, stabilizer or yield point former comprising at least one polymer as claimed in claim 1.

22. A process for stabilizing emulsions and salt-containing emulsions comprising the step of adding at least one polymer as claimed in claim 1 to the emulsion or salt containing emulsion.

* * * * *